United States Patent
Denny et al.

(10) Patent No.: US 7,064,117 B2
(45) Date of Patent: Jun. 20, 2006

(54) ANTI-CANCER 2,3-DIHYDRO-1H-PYRROLO[3,2-F] QUINOLINE COMPLEXES OF COBALT AND CHROMIUM

(75) Inventors: William Alexander Denny, Auckland (NZ); William Robert Wilson, Auckland (NZ); David Charles Ware, Auckland (NZ); Graham John Atwell, Auckland (NZ); Jared Bruce Milbank, Auckland (NZ); Ralph James Stevenson, Auckland (NZ)

(73) Assignee: Auckland Uniservices Limited, Auckland (NZ)

( * ) Notice: Subject to any disclaimer, the term of this patent is extended or adjusted under 35 U.S.C. 154(b) by 0 days.

(21) Appl. No.: 10/470,155

(22) PCT Filed: Jan. 22, 2002

(86) PCT No.: PCT/NZ02/00005

§ 371 (c)(1),
(2), (4) Date: Jan. 29, 2004

(87) PCT Pub. No.: WO02/059122

PCT Pub. Date: Aug. 1, 2002

(65) Prior Publication Data

US 2004/0138195 A1    Jul. 15, 2004

(30) Foreign Application Priority Data

Jan. 24, 2001 (NZ) .................................... 509540

(51) Int. Cl.
*C07D 471/04* (2006.01)
*A61K 31/475* (2006.01)

(52) U.S. Cl. .................... 514/184; 514/185; 546/2; 546/10

(58) Field of Classification Search ................ 546/10, 546/2; 540/452; 514/185, 184
See application file for complete search history.

(56) References Cited

FOREIGN PATENT DOCUMENTS

WO   WO 01/83482 A    11/2001
WO   WO 200183482 A1 *  11/2001

OTHER PUBLICATIONS

Boger et al. J. Org. Chem. 2000, 65:4088-4100.*
Sof'ina et al. Experimental Evaluation of Antitumor Drugs in the USA and USSR and Clinical Correlations. NCI Monograph 55. NIH Publication No. 80-1933 (1980), pp. 76-78.*
Strandtmann et al. J. Med. Chem. (1967), 10(6):1063-1065.*
Boger, et al; "Selective Metal Cation Activation of a DNA Alkylating Agent: Synthesis and Evaluation of Methyl 1,2,9,9a-Tetrahydrocyclopropa[c]pyrido[3,2-e]indol-4-one-7-carboxylate (CPyI)", pp. 4088-4100; Journal of Organic Chemistry, vol. 65, No. 13, (2000).
Boger, D.L., et al; "A New Method of in Situ Activation for a Novel Class of DNA Alkylating Agents: Tunable Metal Cation Complexation and Activation"; *J. Am. Chem. Soc.* ; vol. 122, pp. 6325-6326 (2000) XP002272345.

* cited by examiner

*Primary Examiner*—Zinna Northington Davis
(74) *Attorney, Agent, or Firm*—Nixon & Vanderhye

(57) ABSTRACT

This invention relates to a class of heterocycles and their metal complexes, and is particularly concerned with the use of these compounds in the preparation of prodrugs or as prodrugs that may be activated under hypoxic conditions by enzymes or by therapeutic ionising radiation, in the treatment of cancer. The invention also relates to the use of these heterocycles and the corresponding metal complexes in the preparation of medicaments and to compositions including the heterocycles or their metal complexes and to methods for preparing these compounds.

10 Claims, 2 Drawing Sheets

Figure 2: Hypoxic Selectivity of complex M1 in HT29 cultures

The downwards arrows indicate no colonies recovered.

ANTI-CANCER 2,3-DIHYDRO-1H-PYRROLO[3,2-F]QUINOLINE COMPLEXES OF COBALT AND CHROMIUM

This application is a National Phase of PCT International Application No. PCT/NZ02/00005 filed Jan. 22, 2002 which designated the U.S., and claimed the benefit of priority Application No. NZ 509540, filed Jan. 24, 2001, the contents of which are hereby incorporated by reference in this application.

The present invention relates to novel heterocycles and their metal complexes, and is particularly concerned with the use of these compounds in the preparation of prodrugs or as prodrugs that may be activated under hypoxic conditions by enzymes or by therapeutic ionising radiation, in the treatment of cancer. The present invention also relates to the use of these novel heterocycles and their metal complexes in the preparation of a medicament and to methods for preparing these compounds.

BACKGROUND TO THE INVENTION

Hypoxic regions occur widely in human tumours, and the cells in these regions are relatively resistant to ionising radiation. This leads to frequent recurrence of tumours after radiotherapy, due to the survival of these radioresistant cells. The use of oxygen-mimetic radiosensitizers has also been widely explored, but with mixed success. The existence of such hypoxic regions, restricted essentially to tumour tissue, has resulted in the development of bioreductive prodrugs (hypoxia-activated prodrugs; HAP) capable of being activated by enzymatic reduction only in these hypoxic regions. The majority of these prodrugs are activated to a transient one-electron intermediate in all cells, but this intermediate is re-oxidised by molecular oxygen in normal tissue, allowing activation to a toxic species to occur only in fully hypoxic cells.

The improved targeting ability of modem radiotherapy to deliver ionizing radiation only to the tumour field has suggested the possibility of using the reducing equivalents from this radiation, rather than cellular enzymes, to activate prodrugs (radiation-activated prodrugs; RAP). The activation of these prodrugs would thus be confined to hypoxic regions within the radiation field, providing a double level of selectivity. Such a mechanism of activation has other theoretical advantages over HAP [Wilson et al., Anticancer Drug Design, 13: 663–685, 1998]. These include:
  Lack of collateral activation in partially hypoxic normal tissues (outside the radiation field).
  Use of the whole of the hypoxic tumour volume (including necrotic regions with no active reductases or reducing cofactors) to activate the prodrug.
  Avoidance of dependence on possibly varying enzyme levels, and degree of effectiveness as enzyme substrates.

While there have been many reports on HAP [for example reviews by Denny, Lancet Oncol. 2000, 1, 25–29; Stratford and Workman, Anti-Cancer Drug Design 1998, 13, 519–528; Denny et al., Brit. J. Cancer, 1996, Suppl. 27, 32–38], there has been relatively few reports on RAP. An approach to using therapeutic ionizing radiation to activate a prodrug was reported [Nishimoto et al., J. Med. Chem. 1992, 35, 2711; Mori et al; J. Org. Chem., 2000, 65, 4641–4647; Shibamoto et al., Jpn. J. Cancer Res., 2000, 91, 433–438; Shibamoto et al., Int. J. Rad. Oncol. Biol. Phys., 2001, 49, 407–413], employing radiolytic activation of a 5-fluorouracil (5-FU)-based compounds, such as compound A.

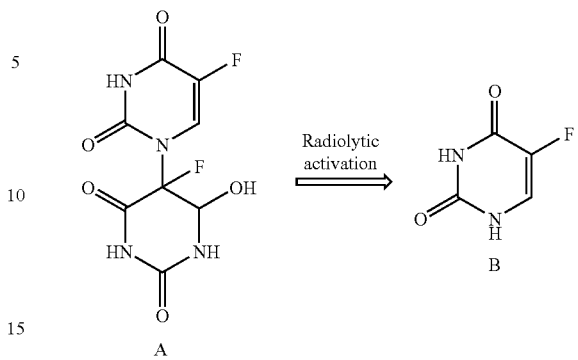

However, doses of radiation used during radiotherapy (typically 2 Gy/day) provide a total primary radical yield of only approximately 1.2 μmol/kg. Only about half of this radical yield comprises reducing species capable of activating prodrugs by reduction. Thus the released effector 5-FU; illustrated as compound B above, is not sufficiently potent to ensure clinically effective concentrations following therapeutic levels of radiation.

The use of metal complexes of bidentate mustards, such as compound C illustrated below, as RAP has also been reported [Denny et al., PCT NZ96/00085, 19 Aug. 1996]. However, the released mustards, such as compound D illustrated below, are also unlikely to be sufficiently potent ($IC_{50}$'s around 1 μM to ensure clinically effective concentrations following therapeutic levels of irradiation.

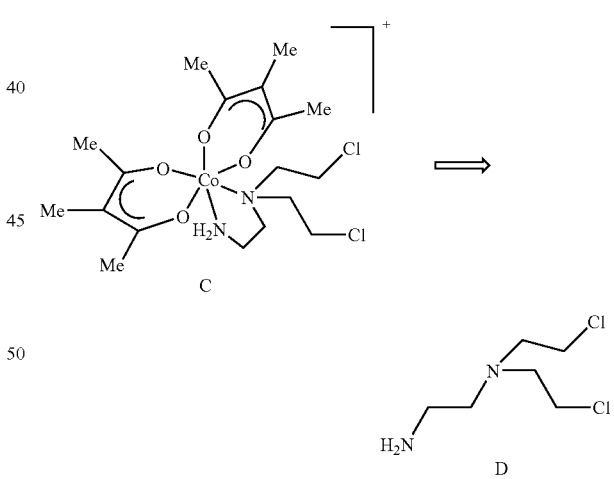

It is therefore an object of the invention to provide heterocycles and their metal complexes either as prodrugs that are activated under hypoxic conditions by enzymes or other endogenous reducing agents or by therapeutic radiation, or at least to provide the public with a useful choice.

SUMMARY OF THE INVENTION

In a first aspect, the present invention provides a class of metal complexes represented by Formula I

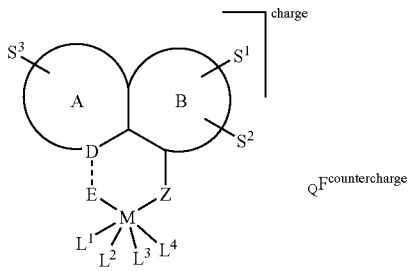

wherein:

A is selected from a 5 or 6 membered aromatic ring system optionally containing one or more heteroatoms and optionally substituted with one or more $C_{1-6}$alkyl, $C_{1-6}$alkoxy, halogen, hydroxy, phosphate, cyano or amino groups;

B is selected from a 5 or 6 membered aromatic ring system optionally containing one or more heteroatoms and optionally substituted with one or more $C_{1-4}$alkyl, $C_{1-6}$alkoxy, halogen, hydroxy, phosphate, cyano or amino groups;

D is selected from C or N;

E is selected from a direct bond, OH or $NR^1{}_2$, where each $R^1$ independently represents H or a $C_{1-6}$alkyl optionally substituted with one or more hydroxy or amino groups, when D represents C; or M is selected from $Co^{III}$, $Co^{II}$, $Cr^{III}$ or $Cr^{II}$;

Z is selected from O, $NR^2$, where $R^2$ represents H or a $C_{1-6}$alkyl optionally substituted with one or more hydroxy or amino groups, $S^1$ and $S^2$ together represent formula V

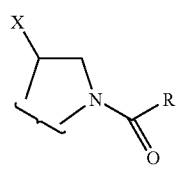

wherein X is selected from a group including $CH_2$-halogen, $CH_2OCO$—($C_1$–$C_6$alkyl optionally substituted with one or more amino or hydroxy groups), $CH_2$-phosphate group or $CH_2OSO_2R^3$, where $R^3$ represents H or a $C_{1-6}$alkyl optionally substituted with one or more hydroxy or amino groups, or $CH_2OSO_2NHR^4$ where $R^4$ represents H or a $C_{1-6}$alkyl optionally substituted with one or more hydroxy or amino groups; and R is selected from one of formulae VI or VII

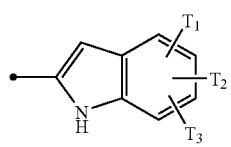

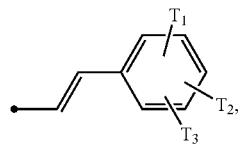

wherein each $T_1$, $T_2$ and $T_3$ is independently selected from H, $OPO(OH)_2$, $OR^5$, $NR^5{}_2$ or $NHCOR^5$, where each $R^5$ independently represents H, a $C_{1-6}$alkyl optionally substituted with one or more hydroxy or amino groups; or
$O(CH_2)_nNR^6{}_2$, where each n is independently 1, 2, 3 or 4 and each $R^6$ is independently selected from H or a $C_{1-6}$alkyl optionally substituted with one or more hydroxy or amino groups and

• represents the point of attachment of R to Formula V defined above, and $S^3$ is selected from H, cyano, phosphate, amino, $C_{1-6}$alkyl, $C_{1-6}$alkoxy, halogen, $CO_2[(C_{1-6}$alkyl) wherein said alkyl is optionally substituted with amino, or hydroxy groups]; $OR^7$, $NR^7{}_2$, or $CONHR^7$, where each $R^7$ independently represents H, a $C_{1-6}$alkyl optionally substituted with one or more hydroxy or amino groups; or $S^3$ represents an optionally substituted 5 or 6 membered cyclic system optionally containing one or more heteroatoms fused to ring system A defined above, wherein said substituents are selected from OH, cyano, phosphate, amino, $C_{1-6}$alkyl, $C_{1-6}$alkoxy, and halogen groups, and wherein ligands $L^1$–$L^4$ are each independently selected in combinations from anionic monodentate ligands, including $CN^-$, $SCN^-$, halide, $NO_3{}^-$; bidentate ligands including MeCOCHJCOMe (Jacac; deprotonated in the complex), where J=H, Me, Cl, SMe, $SO_2Me$, $Me_2NCS_2{}^-$, $S(CH_2)_n$ $SO_3H$, $S(CH_2)_nCO_2H$, $S(CH_2)_nOP(O)(OH)_2$, $CH_2(CH_2)_n$ $SO_3H$, $CH_2(CH_2)_nCO_2H$, $CH_2(CH_2)_nOP(O)(OH)_2$, $S(CH_2)_nP(O)(OH)_2$ or $CH_2(CH_2)_nP(O)(OH)_2$, where n is from 1–4or tridentate ligands VIIIa–VIIIc (=respectively TACH, TAME and TACN when $R_1$–$R_3$=H),

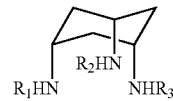

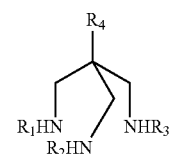

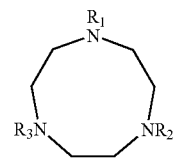

wherein each $R_1$–$R_4$ are independently selected from H, Me, $CH_2(CH_2)_nSO_3H$, $CH_2(CH_2)_nCO_2H$, $CH_2(CH_2)_nP(O)$ $(OH)_2$, $CH_2(CH_2)_nOP(O)(OH)_2$ or $CH_2(CH_2)_nNR^8{}_2$, where each n is independently 1, 2, 3 or 4 and each $R^8$ independently represents H, or a $C_{1-6}$alkyl optionally substituted with one or more hydroxy or amino groups or $L^1$–$L^4$ can also be selected from any one of the tetradentate ligands IX–XVII, or any two of the bidentate ligands XVIII, or any combination of the bidentate ligands XVIII together with any of the monodentate ligands $L^1$–$L^4$ defined above;

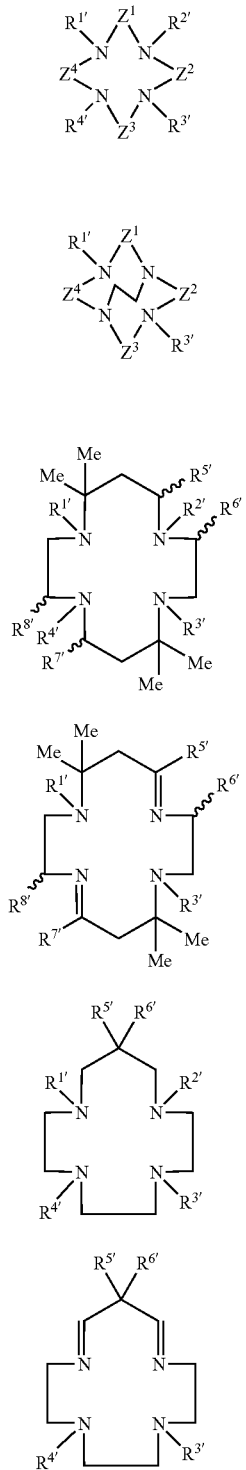

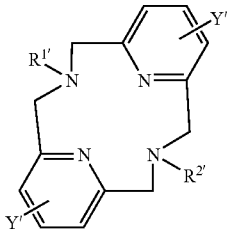

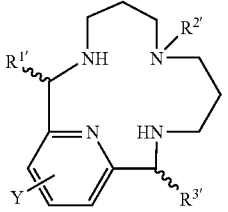

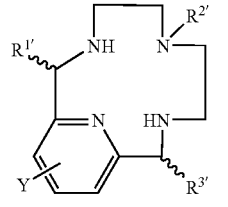

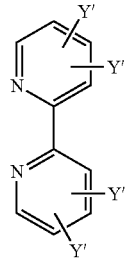

wherein in formulae IX–XVIII, $R^{1'}$ to $R^{8'}$ each independently represent H, Me, $CH_2(CH_2)_nSO_3H$, $CH_2(CH_2)_nCO_2H$, $CH_2(CH_2)_nP(O)(OH)$ or $CH_2(CH_2)_nOP(O)(OH)_2$ or $CH_2(CH_2)_nNMe_2$, where each n is independently 1, 2, 3 or 4;

each $Z^1$–$Z^4$ is independently selected from —$(CH_2)_2$—, —$(CH_2)_3$—, —$CH_2OCH_2$— or —$CH_2N(R^9)CH_2$—; where $R^9$ represents H, a $C_{1-6}$alkyl optionally substituted with one or more hydroxy or amino groups and each Y' is independently selected from H, halogen, $SO_2Me$, $O(C_1-C_6alkyl)$, $NR^{10}_2$, where each $R^{10}$ is independently selected from H or a $C_{1-6}$alkyl optionally substituted with one or more hydroxy or amino groups, or $Q^1(CH_2)_nQ^2$, wherein $Q^1$ is selected from —O—, —$CH_2$—, —NH—, —CONH—, —$CO_2$— or —$SO_2$—, and $Q^2$ is selected from —$CO_2H$, —$SO_3H$, —$OP(O)(OH)_2$ or —$NR^{11}_2$ where each $R^{11}$ is independently selected from H or a $C_{1-6}$alkyl optionally substituted with one or more hydroxy or amino groups; and wherein the overall charge on the complex is neutral, positive or negative and wherein in the case of a non-neutral complex $F^{countercharge}$ is selected from a range of physiologically acceptable-counterions, including halides⁻, NO₃⁻, NH₄⁺ or Na⁺; and wherein q is the required number to neutralise the overall charge on the complex;

and including any enantiomeric or diastereomeric form, and any physiologically salt derivative thereof.

Preferably, the rings A and B of a compound of Formula I as defined above together represent an 8-substituted quinoline system.

In a further aspect the present invention provides a method of providing cancer treatment, which includes the steps of
(a) administering to a patient in need of such therapy an effective amount of a compound of Formula I as defined above, and
(b) activating the compound of Formula I under hypoxic conditions via reduction, either enzymatically or by non-enzymatic endogenous reducing agents, or by ionizing radiation, wherein said activation releases a sufficient amount of an effector from said effective amount of the compound of Formula I.

In a further aspect the present invention further provides a composition comprising as an active agent a compound of Formula I as defined above and a pharmaceutically acceptable excipient, adjuvant or carrier.

In a further aspect the present invention provides the use, in the manufacture of a medicament, of an effective amount of a compound of Formula I for use in treating a subject in need of cancer treatment.

In another aspect, the present invention provides a class of metal complexes represented by Formula Ia

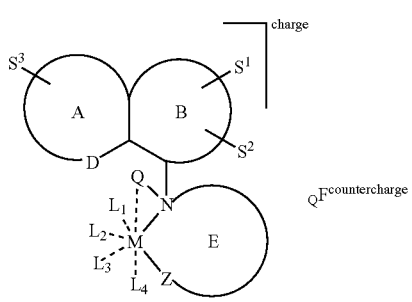

(Ia)

wherein:
A is selected from a 5 or 6 membered aromatic ring system optionally containing one or more heteroatoms and optionally substituted with one or more $C_{1-6}$alkyl, $C_{1-6}$alkoxy, halogen, hydroxy, phosphate, cyano or amino groups;

B is selected from a 5 or 6 membered aromatic ring system optionally containing one or more heteroatoms and optionally substituted with one or more $C_{1-6}$alkyl, $C_{1-6}$alkoxy, halogen, hydroxy, phosphate, cyano or amino groups;

D is selected from C or N;

E is selected from a 5 or 6 membered ring system optionally containing one or more heteroatoms and optionally substituted with one or more $C_{1-6}$alkyl, $C_{1-6}$alkoxy, halogen, hydroxy, phosphate, cyano or amino groups;

M is selected from $Co^{III}$, $Co^{II}$, $Cr^{III}$ or $Cr^{II}$;

Z represents $NH_2$ or NHMe;

Q represents H, $C_{1-6}$alkyl or $(CH_2)_2NH_2$, when Q represents $(CH_2)_2NH_2$, Q will become a ligand for M and replace one of ligands $L^1$–$L^4$ defined below, $S^1$ and $S^2$ together represent formula V

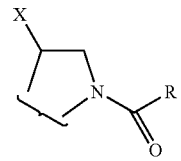

V wherein X is selected from a group including $CH_2$-halogen, $CH_2OCO$—($C_1$–$C_6$alkyl optionally substituted with one or more amino or hydroxy groups), $CH_2$— phosphate group or $CH_2OSO_2R^3$ where $R^3$ represents H or a $C_{1-6}$alkyl optionally substituted with one or more hydroxy or amino groups, or $CH_2OSO_2NHR^4$ where $R^4$ represents H or a $C_{1-6}$alkyl optionally substituted with one or more hydroxy or amino groups; and R is selected from one of formulae VI or VII

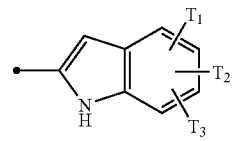

VI

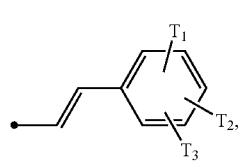

VII wherein each $T_1$, $T_2$ and $T_3$ is independently selected from H, $OPO(OH)_2$, $OR^2$, $NR^2_2$ where each $R^2$ independently represents H, a $C_{1-6}$alkyl optionally substituted with one or more hydroxy or amino groups or $O(CH_2)_nNR^3_2$, where each n is independently 1, 2, 3 or 4, and each $R^3$ is independently selected from H or a $C_{1-6}$alkyl optionally substituted with one or more hydroxy or amino groups and
• represents the point of attachment of R to Formula V defined above, and $S^3$ is selected from H, cyano, phosphate, amino, $C_{1-6}$alkyl, $C_{1-6}$alkoxy, halogen, $CO_2(C_{1-6}$alkyl) wherein said alkyl is optionally substituted with amino, or halogen groups, $OR^4$, $NR^4_2$, $CONHR^4$, where each $R^4$ independently represents H, a $C_{1-6}$alkyl optionally substituted with one or more hydroxy or amino groups; or $S^3$ represents an optionally substituted 4–8 membered cyclic system optionally containing one or more heteroatoms fused to ring system A defined above, wherein said substituents are selected from OH, cyano, phosphate, amino, $C_{1-6}$alkyl, $C_{1-6}$alkoxy, halogen groups, and wherein ligands $L^1$–$L^4$ are each independently selected in combinations from anionic monodentate ligands, including CN⁻, SCN⁻, halide, NO₃⁻; bidentate ligands including MeCOCHJCOMe (Jacac), where J=H, Me, Cl, SMe, $SO_2Me$, $S(CH_2)_nSO_3H$, $S(CH_2)_nCO_2H$, $S(CH_2)_nOP(O)$ (OH)$_2$, CH$_2$(CH$_2$)$_n$SO$_3$H, CH$_2$(CH$_2$)$_n$CO$_2$H or CH$_2$(CH$_2$)$_n$OP(O)(OH)$_2$, where each n is independently 1, 2, 3 or 4; or tridentate ligands VIIIa–VIIIc (=respectively TACH, TAME and TACN when R$_1$–R$_3$=H),

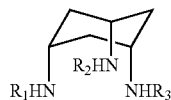

VIIIa

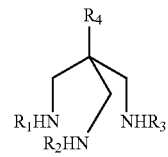

VIIIb

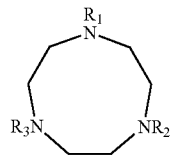

VIIIc wherein R$_1$–R$_4$ are each independently selected from H, Me, CH$_2$(CH$_2$)$_n$SO$_3$H, CH$_2$(CH$_2$)$_n$CO$_2$H or CH$_2$(CH$_2$)$_n$OP(O)(OH)$_2$ or CH$_2$(CH$_2$)$_n$NR$^5$$_2$, where each n is independently 1, 2, 3 or 4 and each R$^5$ independently represents H, or a C$_{1-6}$alkyl optionally substituted with one or more hydroxy or amino groups or L$^1$–L$^4$ can also be selected from any one of the tetradentate ligands IX–XVII, or any two of the bidentate ligands XVIII, or any combination of the bidentate ligands XVIII together with any of the monodentate ligands L$^1$–L$^4$ defined above;

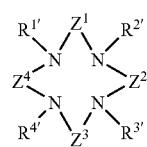

IX

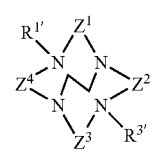

X

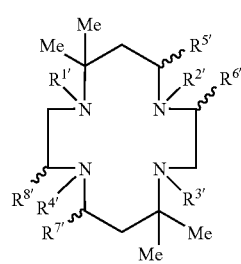

XI

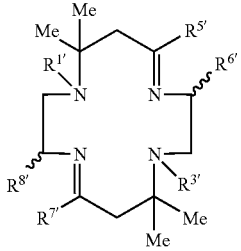

XII

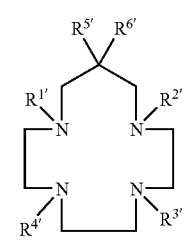

XIII

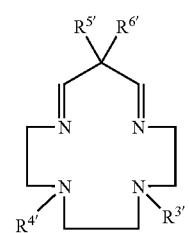

XIV

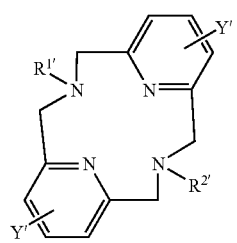

XV

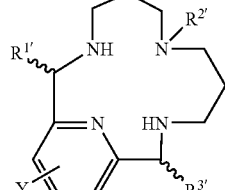

XVI

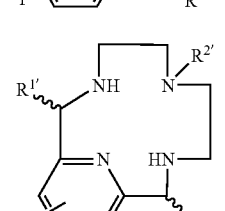

XVII

-continued

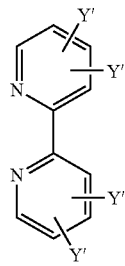

XVIII wherein in formulae IX–XVIII, $R^{1'}$ to $R^{8'}$ each independently represent H, Me, $CH_2(CH_2)_nSO_3H$, $CH_2(CH_2)_nCO_2H$ or $CH_2(CH_2)_nOP(O)(OH)_2$ or $CH_2(CH_2)_nNMe_2$, where each n is independently 1, 2, 3 or 4;

each $Z^{1'}$–$Z^{4'}$ is independently selected from —$(CH_2)_2$—, —$(CH_2)_3$—, —$CH_2OCH_2$— or —$CH_2N(R^6)CH_2$—; where $R^6$ represents H, a $C_{1-6}$alkyl optionally substituted with one or more hydroxy or amino groups and each Y' is independently selected from H, halogen, $SO_2Me$, $O(C_1$–$C_6$alkyl), $NR^7{}_2$, where each $R^7$ is independently selected from H or a $C_{1-6}$alkyl optionally substituted with one or more hydroxy or amino groups, or $Q^1(CH_2)_nQ^2$, wherein $Q^1$ is selected from —O—, —$CH_2$—, —NH—, —CONH—, —$CO_2$— or —$SO_2$—, and $Q^2$ is selected from —$CO_2H$, —$SO_3H$, —$OP(O)(OH)_2$ or —$N^8{}_2$ where each $R^8$ is independently selected from H or a $C_{1-6}$alkyl optionally substituted with one or more hydroxy or amino groups; and wherein the overall charge on the complex is neutral, positive or negative and wherein in the case of a non-neutral complex $F^{countercharge}$ is selected from a range of physiologically acceptable-counterions, including halide$^-$; $NO_3{}^-$, $NH_4{}^+$ or $Na^+$; and wherein q is the required number to neutralise the overall charge on the complex, and including any enantiomeric or diastereomeric form, and any physiologically salt derivative thereof.

Preferably, the rings A and B of a compound of Formula Ia as defined above together represent an 8-substituted quinoline system.

In a further aspect the present invention provides a method of providing cancer treatment, which includes the steps of
(c) administering to a patient in need of such therapy an effective amount of a compound of Formula Ia as defined above, and
(d) activating the compound of Formula Ia under hypoxic conditions via reduction, either enzymatically or by non-enzymatic endogenous reducing agents or ionizing radiation, wherein said activation releases a sufficient amount of an effector, from said effective amount of the compound of Formula Ia, which is of sufficient potency to kill cancer cells.

In a further aspect the present invention further provides a composition comprising as an active agent a compound of Formula Ia as defined above and a pharmaceutically acceptable excipient, adjuvant or carrier.

In a further aspect the present invention provides the use, in the manufacture of a medicament, of an effective amount of a compound of Formula Ia for use in treating a subject in need of cancer treatment.

In another aspect, the present invention provides a class of heterocycles of Formula XIX.

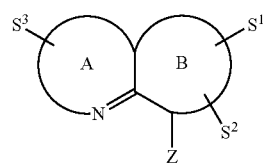

XIX wherein
A is selected from a 5 or 6 membered aromatic ring system optionally containing one or more additional heteroatoms and optionally substituted with one or more $C_{1-6}$alkyl, $C_{1-6}$alkoxy, halogen, hydroxy, phosphate, cyano or amino groups;

B is selected from a 5 or 6 membered aromatic ring system optionally containing one or more heteroatoms and optionally substituted with one or more $C_{1-6}$alkyl, $C_{1-6}$alkoxy, halogen, hydroxy, phosphate, cyano or amino groups;

Z is selected from OH or $NR^1{}_2$, where $R^1$ separately represent H or $C_1$–$C_6$alkyl optionally substituted with one or more amino, hydroxy, a halogen or cyano groups;

$S^1$ and $S^2$ together represent formula V

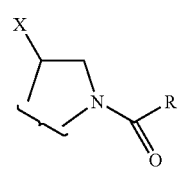

V wherein X is selected from a group including $CH_2$-halogen, $CH_2OCO$—($C_1$–$C_6$alkyl optionally substituted with one or more amino or hydroxy groups), $CH_2$-phosphate group or $CH^2OSO_2R^3$ where $R^3$ represents H or a $C_{1-6}$alkyl optionally substituted with one or more hydroxy or amino groups, or $CH^2OSO_2NHR^4$ where $R^4$ represents H or a $C_{1-6}$alkyl optionally substituted with one or more hydroxy or amino groups; and R is selected from one of formulae VI or VII

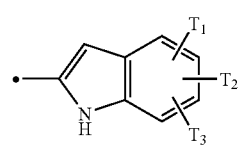

VI

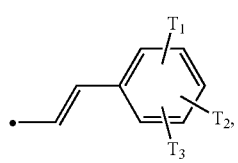

VII wherein each $T_1$, $T_2$ and $T_3$ is independently selected from H, $OPO(OH)_2$, $OR^5$, $NR^5{}_2$ where each $R^5$ independently represents H, a $C_{1-6}$alkyl optionally substituted with one or more hydroxy or amino groups or O(CH$_2$)$_n$NR$^6$$_2$, where each n is independently 1, 2, 3 or 4 and each R$^6$ is independently selected from H or a C$_{1-6}$alkyl optionally substituted with one or more hydroxy or amino groups;

• represents the point of attachment to Formula V defined above;

S$^3$ is selected from H, cyano, phosphate, amino, C$_{1-6}$alkyl, C$_{1-6}$alkoxy, halogen, CO$_2$[(C$_{1-6}$alkyl) wherein said alkyl is optionally substituted with amino, or hydroxy groups], OR$^7$, NR$^7$$_2$, CONHR$^7$ where each R$^7$ independently represents H, a C$_{1-6}$alkyl optionally substituted with one or more hydroxy or amino groups;

or S$^3$ represents an optionally substituted 4–8 membered cyclic system optionally containing one or more heteroatoms fused to ring system A defined above, wherein said substituents are selected from OH, cyano, phosphate, amino, C$_{1-6}$alkyl, C$_{1-6}$alkoxy, and halogen groups, and including any enantiomeric or diastereomeric form, and any physiologically salt derivative thereof.

with the proviso that when Z, A, B, X, S$^1$, S$^2$ and S$^3$ together represent

[chemical structure]

R does not represent one of the following

[chemical structures]

In a further aspect the present invention provides a method of providing cancer treatment, which includes the step of
administering to a patient in need of such therapy an effective amount of a compound of Formula XIX

[chemical structure]  XIX wherein

A is selected from a 5 or 6 membered aromatic ring system optionally containing one or more additional heteroatoms and optionally substituted with one or more C$_{1-6}$alkyl, C$_{1-6}$alkoxy, halogen, hydroxy, phosphate, cyano or amino groups;

B is selected from a 5 or 6 membered aromatic ring system optionally containing one or more heteroatoms and optionally substituted with one or more C$_{1-6}$alkyl, C$_{1-6}$alkoxy, halogen, hydroxy, phosphate, cyano or amino groups;

Z is selected from OH or NR$^1$$_2$, where R$^1$ separately represent H or C$_1$–C$_6$alkyl optionally substituted with one or more amino, hydroxy, a halogen or cyano groups;

S$^1$ and S$^2$ together represent formula V

[chemical structure]  V wherein X is selected from a leaving group including CH$_2$-halogen, CH$_2$-phosphate group, CH$_2$OCO R$^2$, where R$^2$ represents C$_1$–C$_6$alkyl optionally substituted with one or more amino or hydroxy groups; CH$_2$OSO$_2$R$^3$ where R$^3$ represents H or a C$_{1-6}$alkyl optionally substituted with one or more hydroxy or amino groups, or CH$_2$OSO$_2$NHR$^4$ where R$^4$ represents H or a C$_{1-6}$alkyl optionally substituted with one or more hydrogen or amino groups; and R is selected from one of formulae VI or VII

[chemical structure]  VI

[chemical structure]  VII

Preferably, the rings A and B of a compound of Formula XIX as defined above together represent an 8-substituted quinoline system.

wherein each $T_1$, $T_2$ and $T_3$ is independently selected from H, $OPO(OH)_2$, $OR^5$, $NR^5{}_2$ where each $R^5$ independently represents H, a $C_{1-6}$alkyl optionally substituted with one or more hydroxy or amino groups or $O(CH_2)_nNR^6{}_2$, where each n is independently 1, 2, 3 or 4 and each $R^6$ is independently selected from H or a $C_{1-6}$ alkyl optionally substituted with one or more hydroxy or amino groups;

• represents the point of attachment to Formula V defined above;

$S^3$ is selected from H, cyano, phosphate, amino, $C_{1-6}$alkyl, $C_{1-6}$alkoxy, halogen, $CO_2[(C_{1-6}$alkyl$)$ wherein said alkyl is optionally substituted with amino or hydroxy groups], $OR^7$, $NR^7{}_2$, $CONHR^7$ where each $R^7$ independently represents H, a $C_{1-6}$alkyl optionally substituted with one or more hydroxy or amino groups;

or $S^3$ represents an optionally substituted 4–8 membered cyclic system optionally containing one or more heteroatoms fused to ring system A defined above, wherein said substituents are selected from OH, cyano, phosphate, amino, $C_{1-6}$alkyl, $C_{1-6}$alkoxy, and halogen group, and including any enantiomeric or diastereomeric form, and any physiologically salt derivative thereof.

In a further aspect the present invention provides a composition comprising as an active agent a compound of Formula XIX

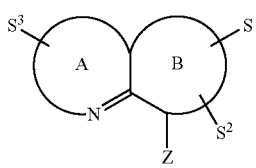

XIX wherein

A is selected from a 5 or 6 membered aromatic ring system optionally containing one or more additional heteroatoms and optionally substituted with one or more $C_{1-6}$alkyl, $C_{1-6}$alkoxy, halogen, hydroxy, phosphate, cyano or amino groups;

B is selected from a 5 or 6 membered aromatic ring system optionally containing one or more heteroatoms and optionally substituted with one or more $C_{1-6}$alkyl, $C_{1-6}$alkoxy, halogen, hydroxy, phosphate, cyano or amino groups;

Z is selected from O or $NR^1$, where $R^1$ represents H or $C_1$–$C_6$alkyl optionally substituted with one or more amino, hydroxy, a halogen or cyano groups;

$S^1$ and $S^2$ together represent formula V

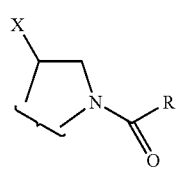

V wherein X is selected from a leaving group including $CH_2$-halogen, $CH_2$-phosphate group, $CH_2OCOR^2$, where $R^2$ represents $C_1$–$C_6$alkyl optionally substituted with one or more amino or hydroxy groups; $CH_2OSO_2R^3$ where $R^3$ represents H or a $C_{1-6}$alkyl optionally substituted with one or more hydroxy or amino groups, or $CH_2OSO_2NHR^4$ where $R^4$ represents H or a $C_{1-6}$alkyl optionally substituted with one or more hydroxy or amino groups; and R is selected from one of formulae VI or VII

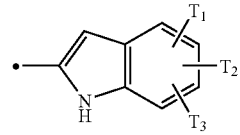

VI

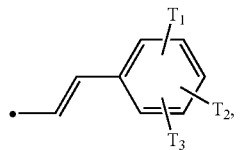

VII wherein each $T_1$, $T_2$ and $T_3$ is independently selected from H, $OPO(OH)_2$, $OR^5$, $NR^5{}_2$ where each $R^5$ independently represents H, a $C_{1-6}$alkyl optionally substituted with one or more hydroxy or amino groups or $O(CH_2)_nNR^6{}_2$, where each n is independently 1, 2, 3 or 4 and each $R^6$ is independently selected from H or a $C_{1-6}$alkyl optionally substituted with one or more hydroxy or amino groups;

• represents the point of attachment to Formula V defined above;

$S^3$ is selected from H, OH, cyano, phosphate, amino, $C_{1-6}$alkyl, $C_{1-6}$alkoxy, halogen, $CO_2[(C_{1-6}$alkyl$)$ wherein said alkyl is optionally substituted with amino, or hydroxy groups], $OR^7$, $NR^7$, $CONHR^7$ where each $R^7$ independently represents H, a $C_{1-6}$alkyl optionally substituted with one or more hydroxy or amino groups;

or $S^3$ represents an optionally substituted 4–8 membered cyclic system optionally containing one or more heteroatoms fused to ring system A defined above, wherein said substituents are selected from OH, cyano, phosphate, amino, $C_{1-6}$alkyl, $C_{1-6}$alkoxy, and halogen groups; and including any enantiomeric or diastereomeric form, and any physiologically salt derivative thereof, and a pharmaceutically acceptable excipient, adjuvant or carrier.

In a further aspect the present invention provides the use, in the manufacture of a medicament, of an effective amount of formula XIX

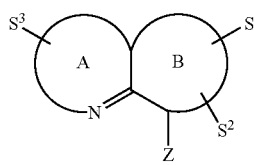

XIX wherein

A is selected from a 5 or 6 membered ring system optionally containing one or more additional heteroatoms and optionally substituted with one or more $C_{1-6}$alkyl, $C_{1-6}$alkoxy, halogen, hydroxy, phosphate, cyano or amino groups;

B is selected from a 5 or 6 membered aromatic ring system optionally containing one or more heteroatoms and optionally substituted with one or more $C_{1-6}$alkyl, $C_{1-6}$alkoxy, halogen, hydroxy, phosphate, cyano or amino groups;

Z is selected from OH or $NR^1{}_2$, where each $R^1$ independently represents H or $C_1$–$C_6$alkyl optionally substituted with one or more amino, hydroxy, a halogen or cyano groups;

$S^1$ and $S^2$ together represent formula V

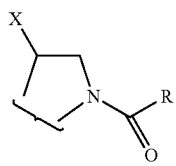

V wherein X is selected from a leaving group including $CH_2$-halogen, $CH_2$-phosphate group, $CH_2OCOR^2$, where each $R^2$ independently represents $C_1$–$C_6$alkyl optionally substituted with one or more amino or hydroxy groups; $CH_2OSO_2R^3$ where $R^3$ represents H or a $C_{1-6}$alkyl optionally substituted with one or more hydroxy or amino groups, or $CH_2OSO_2NHR^5$ where $R^5$ represents H or a $C_{1-6}$alkyl optionally substituted with one or more hydroxy or amino groups; and R is selected from one of formulae VI or VII

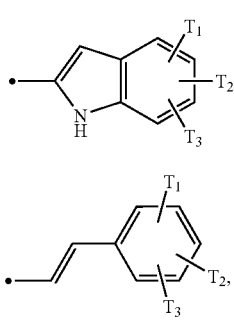

wherein each $T_1$, $T_2$ and $T_3$ is independently selected from H, $OPO(OH)_2$, $OR^5$, $NR^5{}_2$ where each $R^5$ independently represents H, a $C_{1-6}$alkyl optionally substituted with one or more hydroxy or amino groups or $O(CH_2)_nNR^6{}_2$, where each n is independently 1, 2, 3 or 4, and each $R^6$ is independently selected from H or a $C_{1-6}$alkyl optionally substituted with one or more hydroxy or amino groups;

• represents the point of attachment to Formula XIX defined above;

$S^3$ is selected from H, OH, cyano, phosphate, amino, $C_{1-6}$alkyl, $C_{1-6}$alkoxy, halogen, $CO_2[(C_{1-6}$alkyl$)]$ wherein said alkyl is optionally substituted with amino, or hydroxy groups], $OR^7$, $NR^7$, $CONHR^7$ where each $R^7$ independently represents H, a $C_{1-6}$alkyl optionally substituted with one or more hydroxy or amino groups;

or $S^3$ represents an optionally substituted 4–8 membered cyclic system optionally containing one or more heteroatoms fused to ring system A defined above, wherein said substituents are selected from OH, cyano, phosphate, amino, $C_{1-6}$alkyl, $C_{1-6}$alkoxy, and halogen groups, for use in treating a subject in need of cancer treatment, and including any enantiomeric or diastereomeric form, and any physiologically salt derivative thereof.

It is to be recognised that the compounds of the invention defined above can exist in different enantiomeric and/or diastereomeric forms. In such cases it is to be understood that formulae I, Ia and XIX can represent any possible enantiomeric or diastereomeric form, or any mixtures of such forms, and also any physiologically functional salt derivatives thereof.

In a final aspect, the present invention provides methods of preparing compounds of the general formulae I, Ia and XIX defined above. Such methods are described below.

It is to be understood that the terms $C_{1-6}$ alkyl and $C_{1-6}$ alkoxy as used throughout the specification are to be taken as including both the straight and branched forms of such groups.

DESCRIPTION OF THE DRAWINGS

While the invention is broadly defined above, it will be appreciated by those skilled in the art that further aspects of the invention will become apparent with reference to the following Figure and Examples, given by way of example only, wherein.

DETAILED DESCRIPTION OF THE INVENTION

Figure 1:
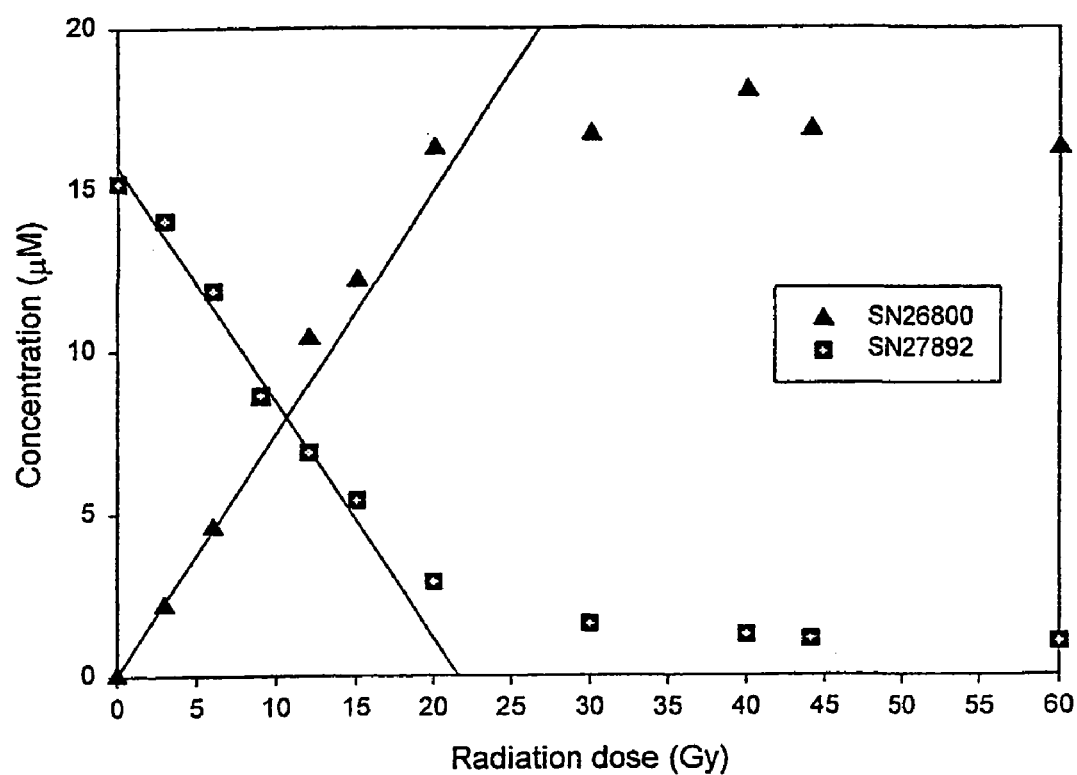
FIG. 1 shows graphically the release of a cytotoxic effector 18a (SN 26800) from a compound of Formula I M1 (SN 27892) when irradiated in formate buffer, pH 7.0 under hypoxic conditions.

As defined above, this invention provides novel heterocycles and their metal complexes, and is particularly concerned with the use of these compounds, as pro drugs activated under hypoxic conditions by enzymes or by therapeutic ionising radiation, in the treatment of cancer.

In order to ensure that the complexes (pro drugs) of Formula I and Ia and the heterocycles (cytotoxins or effectors) of Formula XIX of the present invention are clinically effective, the complexes and heterocycles would preferably have the following properties high chemical stability of the +III metal oxidation states minimal toxicity as a prodrug prior to reductive activation by enzymes or radiation upon activation the prodrug releases a potent cytotoxic or effector unit Examples of pro drug complexes or heterocyclic compounds that fulfil these general criteria include the compounds of Formula I, Ia or XIX as defined above. These compounds can be prepared by the following schemes and processes as described below by way of example only.

PREPARATION EXAMPLE 1

A: Synthesis of 5-hydroxy-2,3-dihydropyrrolo[3,2-f]quinolines

In general, 5-hydroxy-2,3-dihydropyrrolo[3,2-f]quinolines of formula (XIX; Z=O) can be made from the precursor 14, that in turn can be prepared by the method outlined in Scheme 1. Conversion of the known [Curd et al., J. Chem. Soc., 1947, 69, 1613] 1 by the Skraup reaction gives 2 in 80% yield, using an improved procedure [Battersby et al., J. Chem. Soc. Perkin Trans. I, 1979, 2250]. Conversion of methyl to benzyl (2→3→4) (to allow more ready removal at the end of the synthesis), followed by reduction of 4 with Fe/AcOH gives 5. This can be BOC-protected to give 6, which can be iodinated with NIS/MeCN to give 7a or brominated (NBS/MeCN) to give 7b. Alkylation of 7a/7b with 3-bromo-1,1-dimethoxypropane gives 8a/8b, which can be deprotected (TsOH) to 9a/9b, then converted to the vinyl acetates 10a/10b (Ac$_2$O, DMAP, THF, reflux). These undergo radical cyclization (Bu$_3$SnH/AIBN) to give 11, which can be deprotected (Cs$_2$CO$_3$) to give 12. This can be converted either directly (Ph$_3$P, CCl$_4$) or via mesylate 13 (MsCl, Et$_3$N; then LiCl, DMF) to the desired racemic pyrroloquinoline 14.

The benzyl group of 14 can be removed by hydrogenolysis (Scheme 3), and the resulting phenol 16 can be N-deprotected and coupled with appropriate side chains R (formula XIX). An alternative route is by N-deprotection/coupling, followed by removal of the benzyl group (14→17→18), either by hydrogenolysis or by acid treatment.

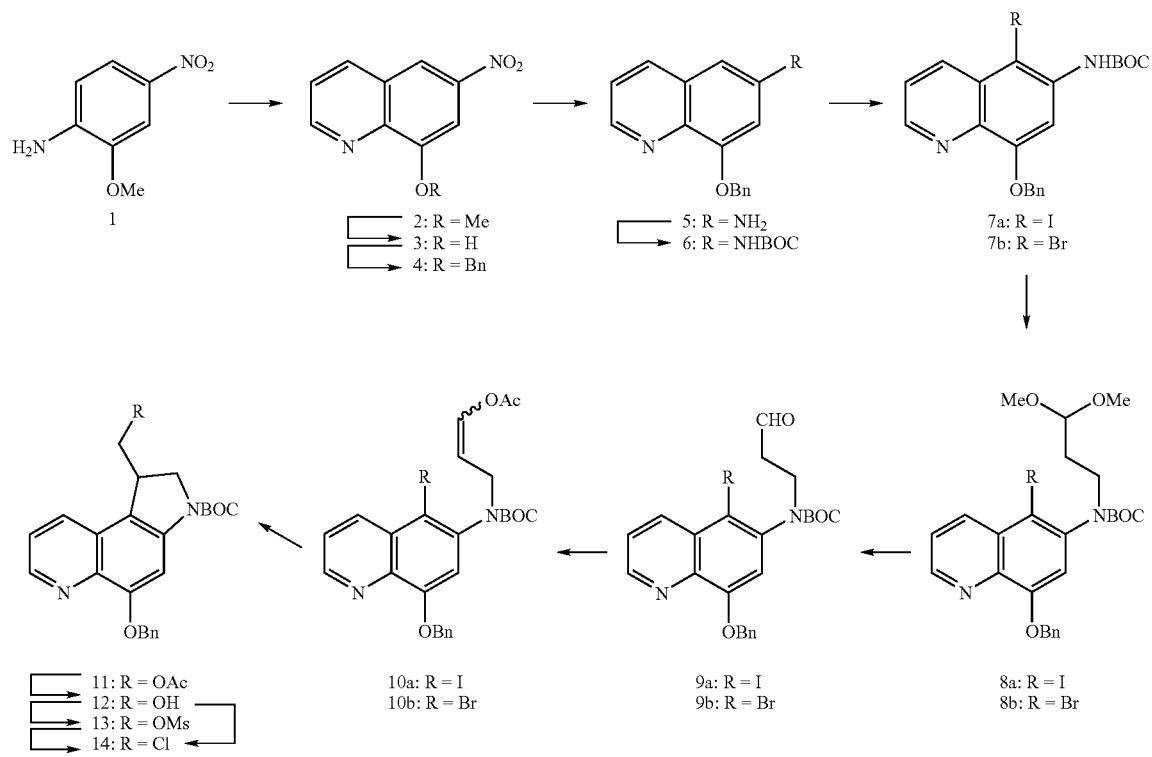

An alternative and shorter route from 7a/7b to 14 is shown in Scheme 2. N-Alkylation of 7a/7b with 1,3-dichloropropene, and radical cyclization of the resulting vinyl chlorides 15a/15b gives 14 in high yield.

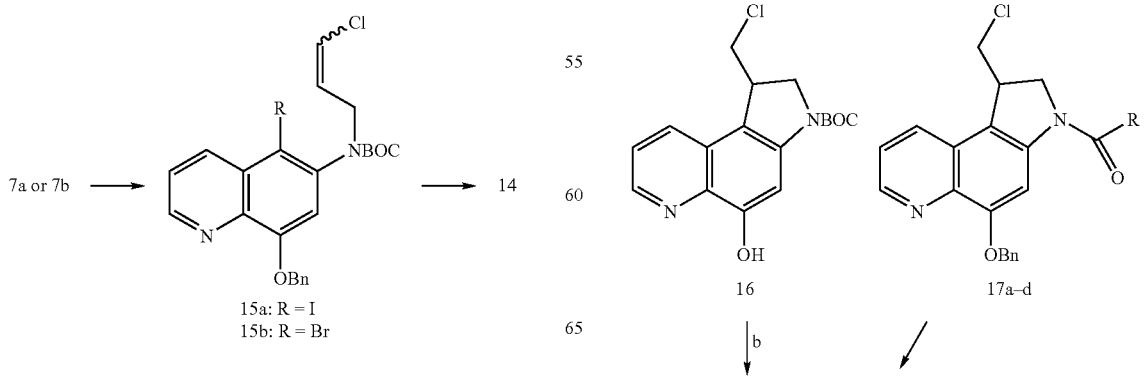

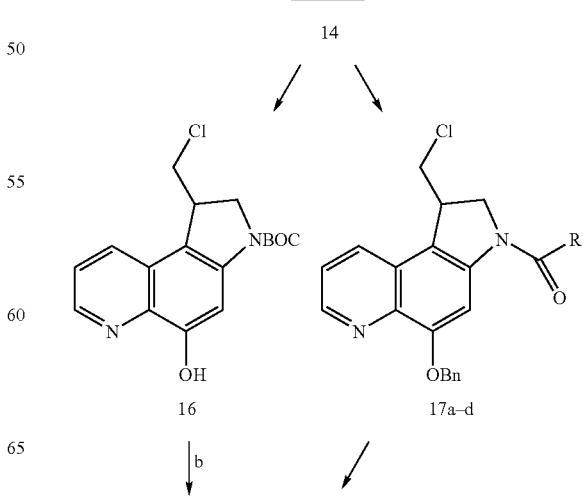

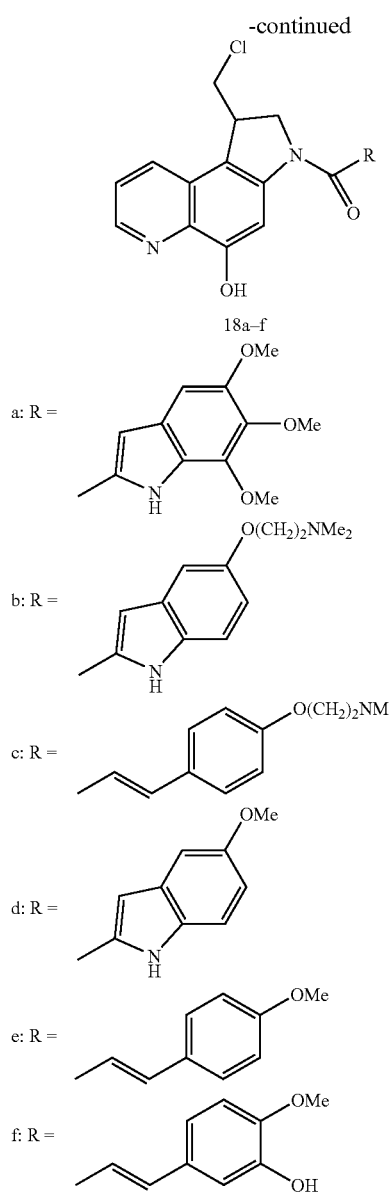

PREPARATION EXAMPLE 2

Synthesis of 5-amino-2,3-dihydropyrrolo[3,2-f]quinolines

In general, 5-amino-2,3-dihydropyrrolo[3,2-f]quinolines (XIX, Z represents $NH_2$) can be prepared from the precursor 25, which can be synthesized by the method outlined in Scheme 4. The quinoline acid 19 [Jung et al., Eur. Pat. Appln. EP 581500 (1994); Chem Abstr, 1994, 122, 205125], prepared by a Skraup reaction on ethyl 4-amino-3-nitrobenzoate, is converted with DPPA/t-BuOH/Et$_3$N to the quinoline 20. Nitro group reduction gives amine 21, which is converted to the phthaloyl derivative 22, and then brominated (NBS/MeCN) to give 23. N-Alkylation of this with 1,3-dichloropropene, followed by radical cyclisation of the resulting chloro intermediate 24 with Bu$_3$SnH/AIBN, gives the tricyclic pyrroloquinolinone 25. As shown in Scheme 4, NBOC deprotection of 25 followed by EDCI coupling with acids gives the compounds of formula 26 (illustrated for the example where R=5,6,7-trimethoxyindol-2-yl). Finally, deblocking of compound 26 by hydrazinolysis gives compounds of formula XIX, where Z represents $NH_2$ (illustrated for the example where R=5,6,7-trimethoxyindol-2-yl; 27).

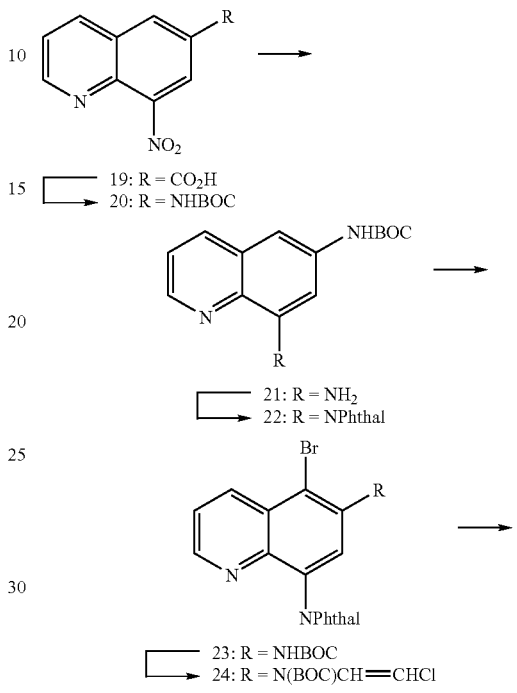

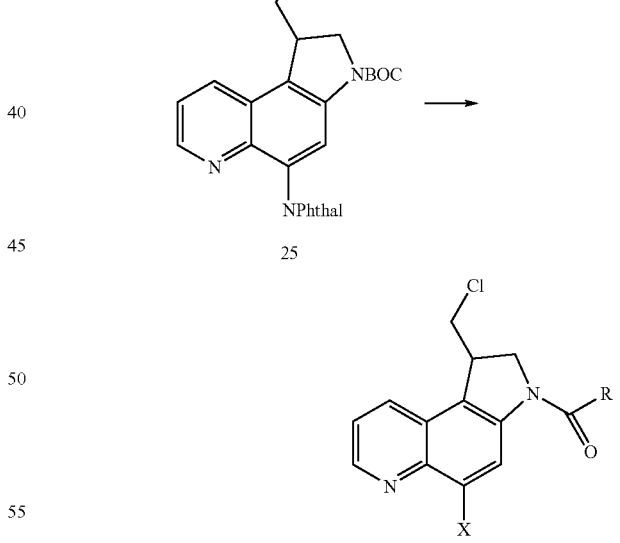

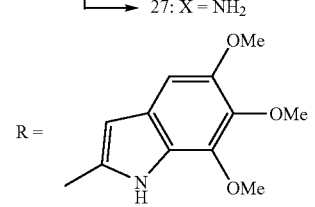

PREPARATION EXAMPLE 3

Synthesis of 5-(2-aminoethylamino)benz[e]indoles

These can be prepared from the appropriate 5-amino compounds by condensation with the BOC-protected aminoacetaldehye, followed by reduction with sodium cyanoborohydride or other suitable reductants, and deprotection of the BOC group. Scheme 5 shows the synthesis of the representative compound 29 from the known [Atwell et al., J. Org. Chem. 1998, 63, 9414–9420] 5-amino compound 28. It will be appreciated that this synthesis can also be applied to the preparation of the analogous derivative from the 5-aminoaza compound 27.

Scheme 5

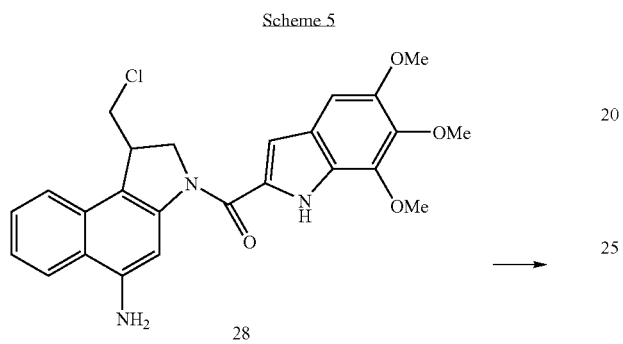

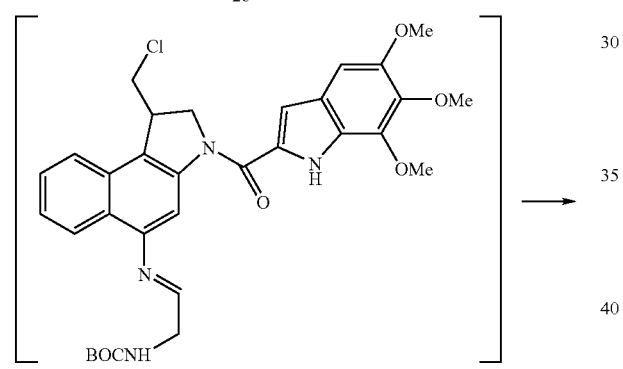

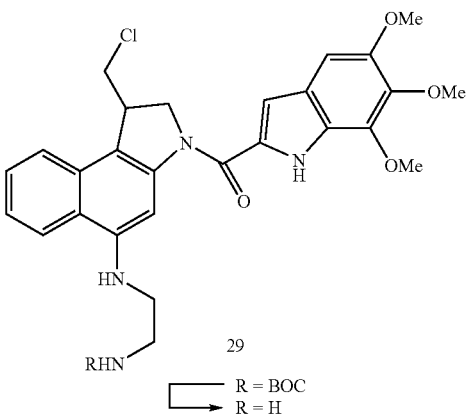

PREPARATION EXAMPLE 4

Synthesis of Ancillary Ligands

As an example of the synthesis of new ancillary cyclen-type tetradentate ligands, reaction of perhydro-3,6,9,12-tetraazacyclopenteno[1,3-f,g]acenaphthylene (30) [Weisman et al, Tetrahedron Lett, 21, 1980, 335] with 1,3-propanesultone gives the bis-quaternary salt (31), which is treated with hydrazine monohydrate to give the bis(propanesulfonic acid) (32) (Scheme 6). It will be appreciated that similar reaction of 30 with other alkylating reagents will give other analogues, such as those represented as compounds 33 to 36 in Scheme 6.

Scheme 6

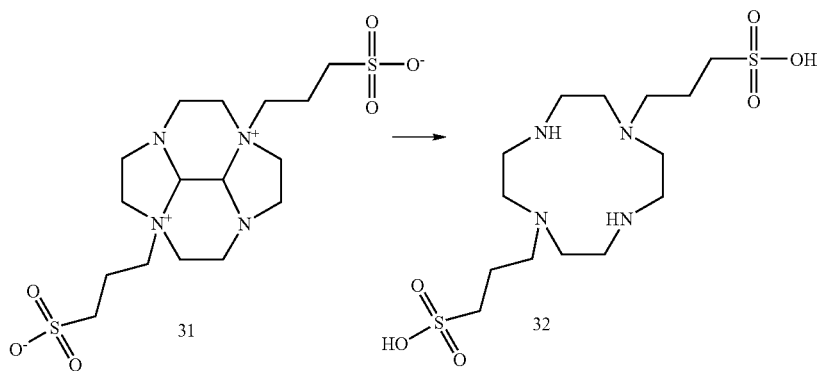

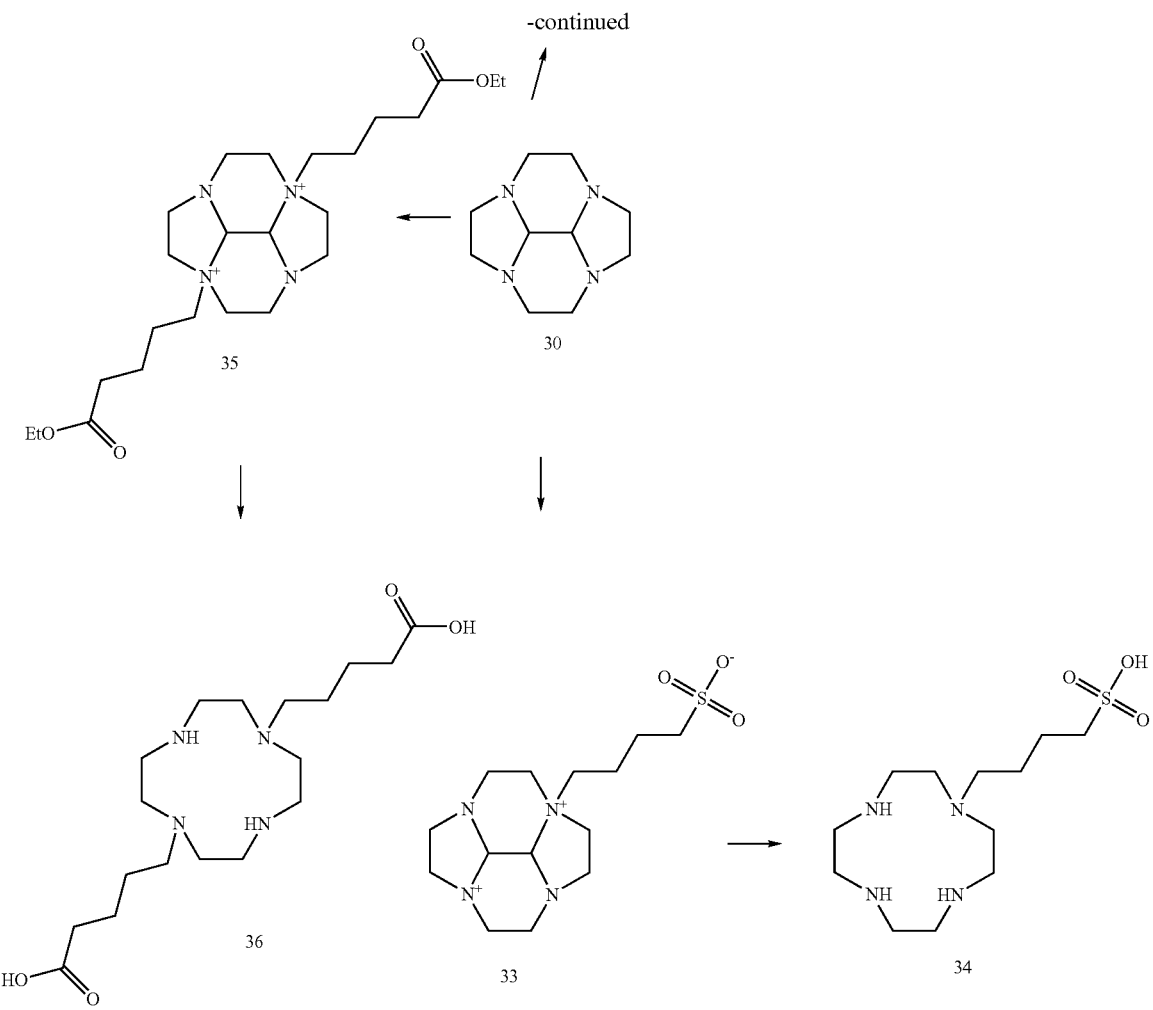

PREPARATION EXAMPLE 5

Synthesis of Metal Complexes

As an example of the synthesis of metal complexes of Formula I defined above, using a tetradentate ancillary ligand, reaction of complex 39 bearing labile triflate ligands with 18a gives the $Co^{III}$ complex M1, as illustrated in Scheme 7.

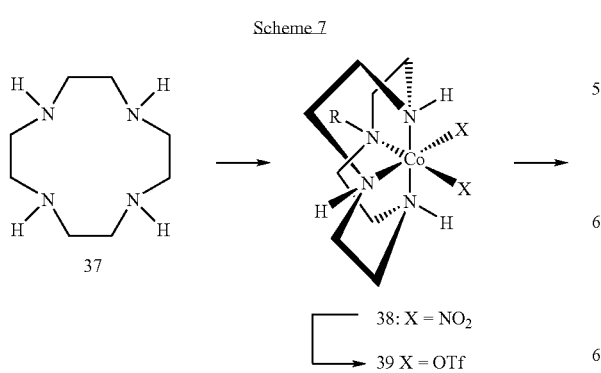

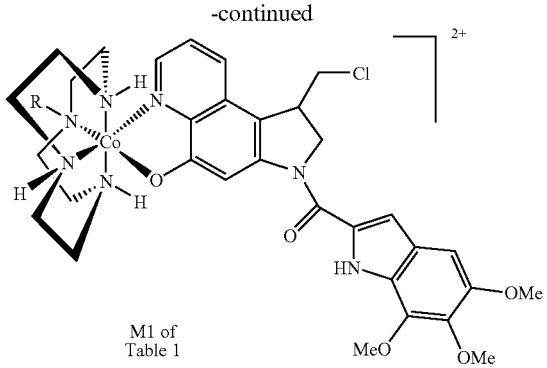

M1 of Table 1

As an example of the synthesis of metal complexes of Formula Ia defined above, using bidentate ancillary ligands, reaction of 18a with $[Cr(acac)_2(H_2O)_2]ClO_4] \cdot 2H_2O$ in dry $CH_3CN$ gives the desired $Cr(acac)_2$-18a complex M4. This reaction pathway is represented in Scheme 8. Similar reaction of 29 gives the corresponding $Cr(acac)_2$-29 complex M6.

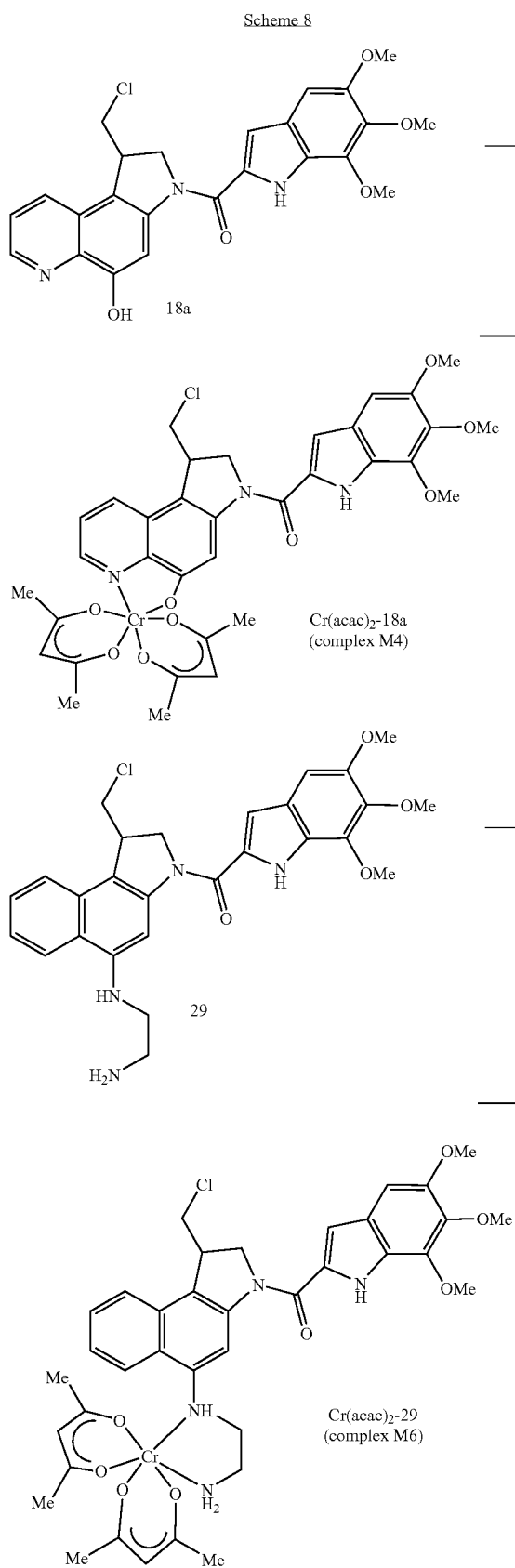

Scheme 8

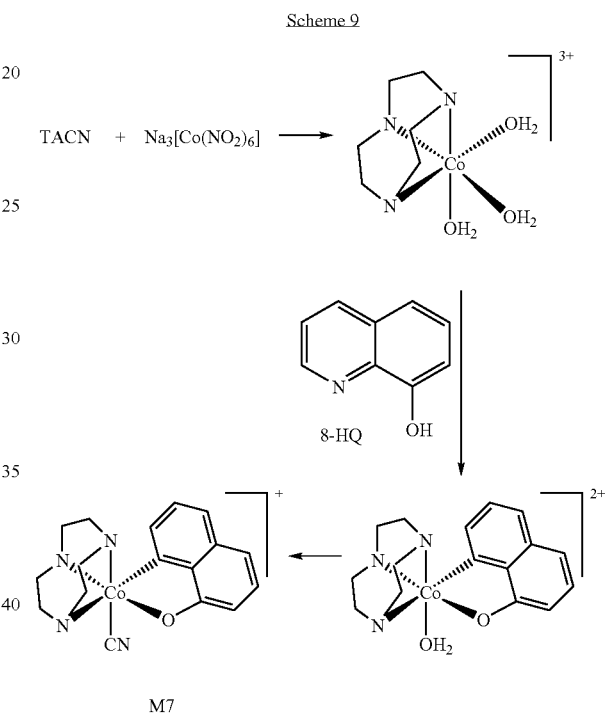

Cr$^{III}$ complexes with other tetradentate macrocycles may be prepared by a similar synthetic route to that employed in the example above using Co$^{III}$, in that the key intermediate for both is a reactive bis[triflato] complex (or a solvent species in solution). The use of nitro complexes as precursors to triflato complexes is unlikely for Cr$^{III}$, as nitro is a poor ligand on Cr$^{III}$. Instead, chloro complexes serve the purpose well. In the strongly acidic triflic acid, protonation of coordinated Cl$^-$ is significant and leads to labilization and ligand loss, made irreversible by removal of the gaseous HCl co-product.

As an example of metal complexes with tridentate ligands, reaction of the triamine TACN with Na$_3$[Co(NO$_2$)$_6$] gives the complex [Co(TACN)(H$_2$O)$_3$].(OTf)$_3$ (Scheme 9). Reaction of this with the model quinoline 8-hydroxyquinline (8-HQ) gives complex M7.

EXAMPLES OF THE INVENTION

The following examples of metal complexes M1–M9 in Table 1 are representative of the complexes of the invention and can be prepared by the detailed processes of the invention described after the table.

Table 1. Structures and Physical Properties of Metal Complexes

| No | Metal | toxic ligand | Ancillary ligands | Analyses |
|---|---|---|---|---|
| M1 | Co$^{III}$ | 18a | Cyclen (IX; Z$^1$–Z$^4$ = –(CH$_2$)$_2$–, R$^{1'}$–R$^{4'}$ = H) | C$_{32}$H$_{41}$N$_7$$^{35}$ClCoO$_5$ [M-2ClO$_4$-H]$^+$ Calc: 697.21897 Fd: 697.21327 |
| M2 | Co$^{III}$ | 18c | Cyclen (IX; Z$^1$–Z$^4$ = –(CH$_2$)$_2$–, R$^{1'}$–R$^{4'}$ = H) | C$_{33}$H$_{45}$$^{35}$ClCoN$_7$O$_3$ [M-2OTf]$^+$ Calc: 681.26044. Fd: 681.26064 |

-continued

| No | Metal | toxic ligand | Ancillary ligands | Analyses |
|---|---|---|---|---|
| M3 | $Co^{III}$ | 18b | Cyclen (IX; $Z^1$–$Z^4$ = – $(CH_2)_2$–, $R^{1'}$–$R^{4'}$ = H) | $C_{33}H_{44}{}^{35}ClCoN_8O_3$ [M-2OTf]$^+$ Calc: 694.25569. Fd: 694.25305 |
| M4 | $Cr^{III}$ | 18a | (Acac)$_2$ (MeCOCH$_2$COMe)$_2$ | $C_{34}H_{36}N_3{}^{35}ClCrO_9$ [M + H]$^+$ Calc: 717.15452 Fd: 717.15198 |
| M5 | $Co^{III}$ | 18a | (Me$_2$dithiocarbamato)$_2$ (Me$_2$NSC$_2$)$_2$ | |
| M6 | $Cr^{III}$ | 29 | (Acac)$_2$ (MeCOCH$_2$COMe)$_2$ | $C_{37}H_{43}N_4{}^{35}ClCrO_8$ [M-ClO$_4$]$^+$ Calc: 758.21745 Fd: 758.21834 |
| M7 | $Co^{III}$ | 8-HQ | TACN (VIIIc: $R^1$–$R^3$ = H)) | |

Example A

Preparation of 1-(chloromethyl)-5-hydroxy-3-[(5,6,7-trimethoxyindol-2-yl)carbonyl]-2,3-dihydro-1H-pyrrolo[3,2-f]quinoline (18a) and Analogues 18b–18f by the Methods of Schemes 1–3

8-Hydroxy-6-nitroquinoline hydrobromide (3). A solution of 8-methoxy-6-nitroquinoline (2) [prepared from 2-methoxy-4-nitroaniline 1 by the method of Battersby et al., J. Chem., Soc. Perkin Trans. 1, 1979, 2550] (50.0 g, 0.245 mol) in 48% aqueous HBr (0.205 L, 1.22 mol) was stirred at reflux for 65 h. The mixture was cooled in ice and the precipitate was removed by filtration and dried in a desiccator to give 3 as the hydrobromide salt (58.0 g, 87%): subl. 140° C., mp>230° C; $^1$H NMR (DMSO) δ 10.69 (br s, 2 H), 9.20 (dd, J=4.9, 1.5 Hz, 1 H), 9.11 (dd, J=8.5, 1.5 Hz, 1 H), 8.64(d, J=2.4 Hz, 1 H), 8.05 (dd, J=8.5, 4.9 Hz, 1 H), 7.90 (d, J=2.4 Hz, 1 H); $^{13}$C NMR (DMSO) δ 152.0, 149.4, 146.4, 144.3, 135.4, 128.3, 124.1, 114.5, 106.5. Anal. Calcd for $C_9H_6N_2O_3$.HBr: C, 40.01; H, 2.61; N, 10.37. Found: C, 40.44; H, 2.17; N, 10.83.

8-Benzyloxy-6-nitroquinoline (4). A mixture of 3 (58.0 g, 0.214 mol), DMF (400 mL), K$_2$CO$_3$ (103.5 g, 0.75 mmol), and NaI (1.60 g, 10.7 mmol) was stirred at room temperature, while benzyl bromide (25.4 mL, 0.214 mmol) was added in four portions at half hourly intervals. A total of 9 h after the first addition, the mixture was poured onto ice (1.5 kg) and the precipitate was removed by filtration, washed with water, and dried. The crude material was dissolved in CH$_2$Cl$_2$ and the solution was filtered through alumina to give 4 (59.55 g, 99%): mp (EtOH) 152–153° C.; $^1$H NMR (CDCl$_3$) δ 9.13 (dd, J=4.2, 1.8 Hz, 1 H), 8.35 (d, J=2.3 Hz, 1 H), 8.29 (dd, J=8.4, 1.8 Hz, 1 H), 7.83 (d, J=2.3 Hz, 1 H), 7.59 (dd, J=8.4, 4.2 Hz, 1 H), 7.56 (d, J=7.6 Hz, 2 H), 7.40 (dd, J=7.6, 7.2 Hz, 2 H), 7.33 (t, J=7.2 Hz, 1 H), 5.50 (s, 2 H); $^{13}$C NMR (CDCl$_3$) δ 155.4, 152.5, 145.6, 142.6, 137.9, 135.4, 128.8, 128.4, 127.8, 127.5, 123.3, 116.3, 103.1, 71.4. Anal. Calcd. for $C_{16}H_{12}N_2O_3$: C, 68.57; H, 4.32; N, 9.99. Found: C, 68.51; H, 4.29; N, 10.04.

6-Amino-8-benzyloxyquinoline (5). Iron dust (16.0 g, 0.285 mol) was added to a solution of 4 (8.00 g, 28.5 mmol) and AcOH (16 mL, 0.285 mol) in EtOH-water (5:1, 240 mL) at reflux. After 10 min, the mixture was carefully poured into saturated aqueous NaHCO$_3$ (300 mL). The mixture was filtered through Celite and the filter cake was washed with water (100 mL), EtOH (3×50 mL), and CH$_2$Cl$_2$ (3×100 mL). The combined filtrates were diluted with water (300 mL) and the aqueous layer was separated and extracted with CH$_2$Cl$_2$ (2×50 mL). The combined extracts were washed with water, dried (Na$_2$SO$_4$), and evaporated to give 5 (7.13 g, 100%) as a tan solid: mp 183–185° C.; $^1$H NMR (CDCl$_3$) δ 8.66 (dd, J=4.2, 1.6 Hz, 1 H), 7.84 (dd, J=8.3, 1.6 Hz, 1 H), 7.48 (dd, J=8.1, 1.7 Hz, 2 H), 7.23–7.39 (m, 3 H), 7.28 (dd, J=8.3, 4.2 Hz, 1 H), 6.51, 6.48 (2×d, J=2.3 Hz, 1 H each), 5.36 (s, 2 H), 3.85 (br s, 2 H); $^{13}$C NMR (CDCl$_3$) δ 155.2, 155.7, 144.8, 136.8, 135.9, 133.5, 130.8, 128.6, 127.8, 127.0, 122.0, 102.6, 100.0, 70.6. Anal. Calcd for $C_{16}H_{14}N_2O$: C, 76.78; H, 5.64; N, 11.19. Found C, 76.54; H, 5.61; N, 11.15.

8-Benzyloxy-6-(tert-butyloxycarbonylamino)quinoline (6). A mixture of 5 (7.63 g, 30.5 mmol), BOC$_2$O (8.65 g, 39.6 mmol) and dioxane (70 mL) was stirred at reflux for 2 h. Further BOC$_2$O (0.86 g, 4.0 mmol) was added and the mixture was heated at reflux for another 1 h. The dioxane was evaporated, the remaining oil was triturated with pentane, and the resulting solid was removed by filtration, dissolved in CH$_2$Cl$_2$ and filtered through alumina to give 6 (10.42 g, 98%) as a cream solid: mp 180–181° C.; $^1$H NMR (CDCl$_3$) δ 8.77 (dd, J=4.2, 1.6 Hz, 1 H), 7.98 (dd, J=8.3, 1.6 Hz, 1 H), 7.55 (d, J=2.1 Hz, 1 H), 7.41 (dd, J=7.4, 2.2 Hz, 2 H), 7.34 (dd, J=8.3, 4.2 Hz, 1 H), 7.20–7.29 (m, 3 H), 7.02 (d, J=2.1 Hz, 1 H), 5.28 (s, 2 H), 1.49 (s, 9 H); $^{13}$C NMR (CDCl$_3$) δ 154.6, 152.7, 147.4, 137.2, 136.8, 136.3, 135.2, 129.9, 128.4, 127.7, 127.2, 122.0, 105.8, 103.5, 80.6, 70.6, 28.2. Anal. Calcd for $C_{21}H_{22}N_2O_3$: C, 71.98; H, 6.33; N, 7.99. Found C, 71.80; H, 6.31; N, 7.98.

8-Benzyloxy-6-(tert-butyloxycarbonylamino)-5-iodoquinoline (7a). A mixture of 6 (1.04 g, 3.0 mmol), NIS (0.70 g, 3.1 mmol) and CH$_3$CN (10 mL) was stirred at reflux for 30 min. Further NIS (40 mg, 0.18 mmol) was added and the mixture stirred at reflux for a further 30 min. The CH$_3$CN was evaporated and the residue was taken up in EtOAc (30 mL) and washed with a solution of Na$_2$S$_2$O$_5$ and Na$_2$CO$_3$ in water (×3). The aqueous washes were back extracted with EtOAc (×2). The combined organic extracts were washed with water, dried (brine, MgSO$_4$), filtered through silica gel, and evaporated to give 7a (1.33 g, 93%), which crystallized from hexane as tan needles: mp 118–119° C.; $^1$H NMR (CDCl$_3$) δ 8.79 (dd, J=4.2, 1.4 Hz, 1 H), 8.32 (dd, J=8.6, 1.4 Hz, 1 H), 8.29 (s, 1 H), 7.59 (dd, J=8.0, 1.7 Hz, 2 H), 7.43 (dd, J=8.6, 4.2 Hz, 1 H), 7.25–7.39 (m, 3 H), 7.24 (br s, 1 H), 5.43 (s, 2 H), 1.57 (s, 9 H); $^{13}$C NMR (CDCl$_3$) δ 155.2, 152.4, 148.1, 139.5, 138.9, 138.3, 136.2, 130.7, 128.5, 128.0, 123.4, 103.9, 81.5, 78.1, 71.0, 28.3. Anal. Calcd for $C_{21}H_{21}IN_2O_3$: C, 52.96; H, 4.44; N, 5.88. Found C, 53.18; H, 4.39; N, 5.95.

8-Benzyloxy-6-[N-(tert-butyloxycarbonyl)-N-(3,3-dimethoxypropyl)amino]-5-iodoquinoline (8a). NaH (60% in oil, 92 mg, 2.3 mmol) under nitrogen was washed with pentane (2×2 mL), cooled (ice-water) and treated with a solution of 7a (1.00 g, 2.10 mmol) in DMF (10 mL) over 5 min. The mixture was allowed to warm to room temperature and stir for 30 min, over which time it became bright yellow and effervescence ceased A solution of 3-bromo-1,1-dimethoxypropane (0.69 g, 3.77 mmol) in DMF (0.5 mL) was added and the mixture was stirred at room temperature for 22 h. The mixture was poured into pH 7.4 phosphate buffer (50 mL) and extracted with EtOAc (3×20 mL). The combined extracts were washed with water (2×50 mL), dried (brine, Na$_2$SO$_4$), evaporated, and purified by dry-flash column chromatography (silica gel, 10–90% EtOAc/hexane), to give 8a (1.00 g, 83%) as a cream powder: mp 120–121° C.; $^1$H NMR (CDCl$_3$) major rotamer δ 8.94 (br d, J=2.9 Hz, 1 H), 8.52 (dd, J=8.6, 1.5 Hz, 1 H), 7.45–7.58 (m, 3 H), 7.25–7.40 (m, 3 H), 6.96 (br s, 1 H), 5.46 (s, 2 H), 4.40 (t, J=4.7 Hz, 1 H), 3.84 (br ddd, J=14.6, 7.3, 7.3 Hz, 1 H), 3.33 (ddd, J=14.6, 8.2, 5.8 Hz, 1 H), 3.28, 3.25 (2×s, 3 H each), 1.65–1.95 (m, 2 H), 1.23 (br s, 9 H); $^{13}$C NMR (CDCl$_3$) major rotamer δ 154.6, 153.6, 149.9, 143.8, 141.3, 139.8, 136.0, 131.2, 128.7, 128.0, 127.0, 123.4, 112.3, 102.9, 93.3, 80.3, 70.9, 53.1, 52.7, 45.4, 31.2, 28.1; C$_{26}$H$_{31}$IN$_2$O$_5$ requires M$^+$. 578.1278. Found 578.1257.

8-Benzyloxy-6-[N-(tert-butyloxycarbonyl)-N-(3-oxopropyl)amino]-5-iodoquinoline (9a). A solution of 8a (0.75 g, 1.30 mmol), TsOH·H$_2$O (0.12 g, 0.65 mmol) and water (3.75 mL) in acetone (38 mL) was stirred at reflux for 2.25 h. Most of the acetone was evaporated and the residue was diluted with water (50 mL) and saturated aqueous NaHCO$_3$ (5 mL) and extracted with EtOAc (3×20 mL). The combined extracts were washed with water (2×50 mL), dried (Na$_2$SO$_4$), and evaporated to give 9a (0.68 g, 99%) as a pale yellow foam; $^1$NMR (CDCl$_3$) major rotamer δ 9.68 (s, 1 H), 8.97 (dd, J=4.2, 1.5 Hz, 1 H), 8.51 (dd, J=8.6, 1.5 Hz, 1 H), 7.53 (dd, J=8.6, 4.2 Hz, 1 H), 7.47–7.55 (m, 2 H), 7.25–7.40 (m, 3 H), 6.87 (br s, 1 H), 5.49 (s, 2 H), 4.17 (br dt, J=14.5, 7.1 Hz, 1 H), 3.59 (dt, J=14.5, 6.5 Hz, 1 H), 2.57 (br dd, J=7.1, 6.5 Hz, 2 ), 1.23 (s, 9 H); $^{13}$C NMR (CDCl$_3$) major rotamer δ 200.3, 154.8, 153.4, 150.0, 143.0, 141.0, 139.7, 135.9, 131.0, 128.6, 127.9, 127.0, 123.4, 112.1, 93.1, 80.7, 70.7, 42.9, 42.5, 27.9; C$_{24}$H$_{25}$IN$_2$O$_4$ requires M$^+$. 532.0859. Found 532.0862.

6-[N-(3-Acetoxy-2-propenyl)-N-(tert-butyloxycarbonyl) amino]-8-benzyloxy-5-iodoquinoline (10a). A mixture of 9a (0.62 g, 1.16 mmol), Et$_3$N (0.40 mL, 2.87 mmol), Ac$_2$O (0.25 mL, 2.65 mmol), DMAP (14 mg, 0.11 mmol), and THF (12 mL) was stirred at reflux for 2 h. Further Et$_3$N (0.80 mL, 5.74 mmol), Ac$_2$O (0.50 mL, 5.3 mmol), and DMAP (10 mg, 0.08 mmol) were added and heating was continued for a further 2 h. The solvent was evaporated, and the residue was diluted with pH 7.4 phosphate buffer (50 mL) and extracted with EtOAc (3×20 mL). The combined extracts were washed with water (50 mL), dilute aqueous NaHCO$_3$ (50 mL), and water (50 mL) before being dried (brine, Na$_2$SO$_4$), and evaporated. The residue was purified by dry-flash column chromatography (silica gel, 10–80% EtOAc-hexane) to give 10a (0.54 g, 81%) as a white foam, which contained a 1:4 mixture of Z and E isomers: $^1$H NMR (CDCl$_3$) major rotamer δ 8.94 (br s, 1 H), 7.45–7.55 (m, 3 H), 7.27–7.40 (m, 3 H), 6.84–7.12 (m, 2 H), 5.36–5.58 (m, 2.8 H), 4.91 (ddd, J=7.6, 6.5, 5.9 Hz, 0.2 H), 4.57 (dd, J=15.0, 5.9 Hz, 0.2 H), 4.39 (dd, J=14.7, 6.8 Hz, 0.8 H), 4.06 (dd, J=15.0, 7.6 Hz, 0.2 H), 3.86 (dd, J=14.7, 7.9 Hz, 0.8 H), 2.08 (s, 2.4 H), 1.88 (s, 0.6 H), 1.57 (br s, 1.8 H), 1.26 (br s, 7.2 H); $^{13}$C NMR (CDCl$_3$) major rotamer δ 167.4, 167.0, 154.5, 149.8, 154.3, 149.8, 153.3, 142.8, 140.9, 139.7, 138.8, 139.7, 143.1, 135.8, 130.9, 136.0, 127.8, 126.8, 126.7, 128.4, 123.2, 112.1, 112.0, 109.1, 108.2, 93.5, 93.1, 80.9, 80.4, 70.8, 70.7, 46.4, 42.7, 27.9, 28.1, 20.3, 20.1; C$_{26}$H$_{27}$IN$_2$O$_5$ requires M$^+$. 574.0965. Found 574.0962.

1-(Acetoxymethyl)-5-benzyloxy-3-(tert-butyloxycarbonyl)-2,3-dihydro-1H-pyrrolo[3,2-f]quinoline (11). A solution of 10a (0.54 g, 0.94 mmol), AIBN (15 mg, 0.09 mmol), and Bu$_3$SnH (0.32 g, 1.13 mmol) in benzene (45 mL) was stirred at reflux under nitrogen for 5.5 h. The solvent was evaporated, the residue was triturated with pentane, and the precipitate was collected by filtration to give 11 (0.32 g, 77%), which crystallized from MeOH as fluorescent pale yellow rectangular plates: mp 172–173° C.; $^1$H NMR (CDCl$_3$) δ 8.82 (dd, J=4.1, 1.4 Hz, 1 H), 8.14 (dd, J=8.4, 1.4 Hz, 1 H), 8.07 (br S, 1 H), 7.55 (br s, 2 H), 7.41 (dd, J=8.4, 4.1 Hz, 1 H), 7.36 (dd, J=7.3,7.3 Hz, 2 H), 7.30 (tt, J=7.3, 2.4 Hz, 1 H), 5.44, 5.39 (2×d, J=12.5 Hz, 1 H each), 4.42–4.52 (m, 1 H), 4.05–4.14 (m, 2 H), 3.82–3.93 (m, 2 H), 2.08 (s, 3 H), 1.57 (s, 9 H); $^{13}$C NMR (CDCl$_3$) δ 171.0, 155.2, 152.3, 146.9, 142.0 (br), 137.0, 136.3, 131.1, 128.5, 127.9, 127.7, 126.0, 122.1, 113.3 (v. br), 100.4 (br), 81.4 (br), 70.7, 65.8, 52.6, 37.7, 28.4, 20.9. Anal. Calcd for C$_{26}$H$_{28}$N$_2$O$_5$: C, 69.63; H, 6.29; N, 6.25. Found: C, 69.46; H, 6.27; N, 6.30.

5-Benzyloxy-3-(tert-butyloxycarbonyl)-1-(hydroxymethyl)-2,3-dihydro-1H-pyrrolo[3,2-f]quinoline (12). A mixture of 11 (0.22 g, 0.50 mmol), Cs$_2$CO$_3$ (0.42 g, 1.29 mmol), and EtOH-water (2:1, 6 mL) was stirred at reflux for 30 min. The mixture was diluted with EtOAc (30 mL) and dilute aqueous NaHCO$_3$ (50 mL). The separated aqueous phase was extracted with EtOAc (30 mL). The combined extracts were washed with water (3×50 mL), dried (brine, Na$_2$SO$_4$), and evaporated to give 12 (0.19 g, 95%), which crystallized from MeOH as tiny white needles: mp 170–171° C.; $^1$H NMR (CDCl$_3$) δ 8.54 (br s, 1 H), 7.99 (br d, J=8.0 Hz, 1 H), 7.91 (br s, 1 H), 7.55 (d, J=6.6 Hz, 2 H), 7.20–7.40 (m, 4 H), 5.29 (s, 2 H), 4.00–4.22 (m, 2 H), 3.65–3.78 (m, 3 H, H-1), 3.23 (br s, 1 H), 1.56 (s, 9 H); $^{13}$C NMR (CDCl$_3$) δ 154.4, 152.5 (br), 146.2 (br), 142.2 (v. br), 136.3, 136.2, 131.3, 128.5, 128.0 (v. br), 127.9, 125.9, 121.6, 114.7 (v. br), 100.4 (br), 81.0 (br), 70.7, 64.6, 52.3, 40.9 (br), 28.4. Anal. Calcd. for C$_{24}$H$_{26}$N$_2$O$_4$·H$_2$O: C, 67.91; H, 6.65; N, 6.60. Found: C, 68.16; H, 6.47; N, 6.71.

5-Benzyloxy-1-(methylsulfonyloxymethyl)-3-(tert-butyloxycarbonyl)-2,3-dihydro-1H-pyrrolo[3,2-f]quinoline (13). MsCl (0.06 mL, 0.7 mmol) was added to a cooled (ice-water) solution of 12 (0.17 g, 0.41 mmol) and Et$_3$N (0.2 mL, 1.4 mmol) in CH$_2$Cl$_2$ (3 mL) and the mixture was stirred for 30 min. The CH$_2$Cl$_2$ was evaporated and the residue was stirred with water (25 mL) for 10 min. The mixture was extracted with EtOAc (2×25 mL). The combined extracts were washed with water (2×50 mL), dried (Na$_2$SO$_4$), and evaporated to give 13 (0.17 g, 86%), which crystallized from MeOH as tiny cream needles: mp 156–157° C.; $^1$H NMR (CDCl$_3$) δ 8.80 (dd, J=4.2, 1.4 Hz, 1 H), 8.02 (dd, J=8.7, 1.4 Hz, 1 H 7.97 (br s, 1 H), 7.55 (br d, J=6.9 Hz, 2 H), 7.41 (dd, J=8.7, 4.2 Hz), 7.25–7.38 (m, 3 H), 5.40 (s, 2 H), 4.46 (dd, J=9.8, 3.7 Hz, 1 H), 3.93–4.24 (m, 4 H), 2.90 (s, 3 H), 1.57 (s, 9 H); $^{13}$C NMR (CDCl$_3$) δ 155.6, 152.1, 147.0, 141.0 (v. br), 137.1, 136.1, 130.5, 128.4, 127.9, 127.6 (br), 125.7, 122.3, 112.7 (v. br), 100.3, 81.6 (br), 70.7, 69.9, 52.0, 38.2 (br), 37.4, 28.3. Anal. Calcd for C$_{25}$H$_{28}$N$_2$O$_6$S: C, 61.97; H, 5.82; N, 5.78; S, 6.62. Found: C, 62.15; H, 5.96; N, 5.88; S, 6.54.

5-Benzyloxy-3-(tert-butyloxycarbonyl)-1-(chloromethyl)-2,3-dihydro-1H-pyrrolo[3,2-f]quinoline (14). Method 1. A mixture of 13 (50 mg, 0.10 mmol), LiCl (25 mg, 0.59 mmol), and DMF (0.25 mL) was stirred at 80° C. for 1 h, before ice (3 g) was added. The precipitate was removed by filtration, washed with water, and taken up in EtOAc (20 mL). This solution was washed with water (20 mL), dried (Na$_2$SO$_4$), and evaporated to give 14 (39 mg, 89%), which crystallized from MeOH as fluorescent cream needles: mp 178–179° C.; $^1$H NMR (CDCl$_3$) δ 8.82 (dd, J=4.2, 1.5 Hz, 1 H), 8.05 (br s, 1 H), 7.99 (br d, J=8.4 Hz, 1 H), 7.55 (br s, 2 H), 7.41 (dd, J=8.4, 4.2 Hz, 1 H), 7.35 (dd, J=7.3, 7.3 Hz, 2 H), 7.30 (tt, J=7.3, 2.4 Hz, 1 H), 5.42, 5.38 (2×d, J=12.4 Hz, 1 H each), 4.23 (br d, J=11.7 Hz, 1 H), 4.12 (dd, J=11.7, 8.9 Hz, 1 H), 3.92 (dddd, J=10.1, 8.9, 3.2, 2.6 Hz, 1 H), 3.81 (dd, J=11.1, 3.2 Hz, 1 H), 3.45 (dd, J=11.1, 10.1 Hz, 1 H), 1.56 (s, 9 H); $^{13}$C NMR (CDCl$_3$)δ 155.5, 152.3, 146.9, 141.9(br), 137.1, 136.3, 130.3, 128.5, 127.9, 127.7 (br), 125.6, 122.2, 113.4 (v. br), 100.4 (br), 81.6 (br), 70.8, 53.0, 46.3, 41.1, 28.4. Anal. Calcd. for $C_{24}H_{25}ClN_2O_3$: C, 67.84; H, 5.93; Cl, 8.34; N, 6.59. Found: C, 67.85; H, 5.94; N, 6.68; Cl, 8.26.

8-Benzyloxy-6-[N-(tert-butyloxycarbonyl)-N-(3-chloro-2-propenyl)amino]-5-iodoquinoline (15a). NaH (60% dispersion in oil, 0.26 g, 6.5 mmol) under nitrogen was washed with pentane (3×2 mL), cooled (ice-water), and treated with a solution of 7a (2.80 g, 5.88 mmol) in DMF (28 mL) over 5 min. The cooling bath was removed and the mixture was allowed to stir for 30 min, by which time the solution was deep yellow and effervescence had ceased. 1,3-Dichloropropene (0.98 g, 8.82 mmol) was added and the mixture was stirred for 86 h The mixture was diluted with water (150 mL) and extracted with EtOAc (4×25 mL). The combined extracts were washed with water (3×100 mL), dried (brine, Na$_2$SO$_4$), and evaporated. The residue was triturated with pentane and the precipitate was collected by filtration to give 15a (3.02 g, 93%) as a tan powder: mp 115–135° C. containing a 1:1 mixture of Z and E isomers; $^1$H NMR (CDCl$_3$) major rotamer δ 8.95 (br s, 1 H), 8.50 (dd, J=8.4, 2.5 Hz, 1 H), 7.46–7.55 (m, 3 H), 7.27–7.41 (m, 3 H), 6.79–6.96 (m, 1 H), 5.30–6.03 (m, 4 H), 4.54 (dd, J=15.5, 5.6 Hz, 0.5 H), 4.38 (dd, J=14.8, 6.8 Hz, 0.5 H), 4.18 (dd, J=15.5, 6.9 Hz, 0.5 H), 3.79 (dd, J=14.8, 7.8 Hz, 0.5 H), 1.23–1.82 (m, 9 H); $^{13}$C NMR (CDCl$_3$) major rotamer δ 154.7, 155.2, 153.6, 153.3, 150.2, 150.1, 143.2, 142.8, 141.2, 140.2, 136.2, 136.0, 131.13, 131.08, 128.79, 128.73, 128.12, 127.99, 127.2, 126.6, 126.98, 126.90, 123.5, 123.4, 122.0, 121.1, 112.2, 111.9, 93.65, 93.58, 80.90, 80.85, 71.0, 70.9, 48.8, 45.4, 28.4, 28.1. $C_{24}H_{24}ClIN_2O_3$ requires M$^+$. 550.0520, 552.0491. Found 550.0536, 552.0503. Purification of the mother liquors by dry-flash column chromatography (silica gel, 10–60% EtOAc-hexane) gave further 15a (0.14 g, 4%).

Compound 14 by Method 2. A solution of 15a (3.90 g, 5.45 mmol), AIBN (89 mg, 0.54 mmol), and Bu$_3$SnH (1.75 g, 6.0 mmol) in benzene (270 mL) was heated at reflux under nitrogen for 3 h. The benzene was evaporated, the residue was triturated with pentane, and the precipitate was collected by filtration to give 14 (2.21 g, 95%), identical to the material prepared above.

Compound 14 by Method 3. A mixture of 12 (19 mg, 0.047 mmol), Ph$_3$P (37 mg, 0.14 mmol) and CH$_2$Cl$_2$ (0.4 mL) was treated with CCl$_4$ (0.05 mL, 0.52 mmol), and the mixture was stirred under nitrogen for 4 h. The mixture was diluted with dilute aqueous NaHCO$_3$ (5 mL) and extracted with EtOAc (3×5 mL). The combined extracts were dried (Na$_2$SO$_4$), evaporated, and purified by dry-flash column chromatography (silica gel, 10–90% EtOAc/hexane) to give 14 (20 mg, 100%) identical with the material prepared above.

3-(tert-Butyloxycarbonyl)-1-(chloromethyl)-5-hydroxy-2,3-dihydro-1H-pyrrolo[3,2-f]quinoline (16). A cooled (ice-water) mixture of 14 (0.11 g, 0.27 mmol), 10% Pd/C (55 mg), and TBF (5 mL) under nitrogen was treated with 25% aqueous NH$_4$HCO$_3$ (0.67 mL). The mixture was stirred at 0° C. for 6 h, and was then diluted with EtOAc (20 mL), dried (Na$_2$SO$_4$), filtered through Celite, evaporated, and purified by dry-flash column chromatography (silica gel, 10–50% EtOAc/hexane) to give 16 (39 mg, 44%) as a white solid: mp 148–149° C.; $^1$H NMR (CDCl$_3$) δ 8.61 (dd, J=4.2, 1.2 Hz, 1 H),8.01 (dd, J=8.5, 1.2 Hz, 1 H), 7.83 (br s, 1 H), 7.41 (dd, J=8.5, 4.2 Hz, 1 H), 4.26 (dd, J=11.8, 2.2 Hz, 1 H), 4.14 (dd, J=11.8, 8.5 Hz, 1 H), 3.93 (dddd, J=9.8, 8.5, 3.2, 2.2 Hz, 1 H), 3.80 (dd, J=11.1, 3.2 Hz, 1 H), 3.46 (dd, J=11.1, 9.8 Hz, 1 H), 1.61 (s, 9 H); $^{13}$C NMR (CDCl$_3$) δ 153.5, 152.3, 145.3, 142.4 (br), 135.0, 130.6, 124.9, 122.6, 112.4 (v. br), 100.0, 81.7 (br), 53.0, 46.5, 40.9, 28.4. $C_{17}H_{19}ClN_2O_3$ requires M$^+$. 334.1084, 336.1055. Found 334.1081, 336.1058.

5-Benzyloxy-1-(chloromethyl)-3-(5,6,7-trimethoxyindol-2-ylcarbonyl)-2,3-dihydro-1H-pyrrolo[3,2-f]quinoline (17a). A suspension of 14 (0.65 g, 1.53 mmol) in dioxane (40 mL) was saturated with HCl, allowed to stand for 1 h, and evaporated. 5,6,7-Trimethoxyindole-2-carboxylic acid (0.38 g, 1.53 mmol), EDCI (0.88 g, 4.6 mmol) and DMA (25 mL) were added to the remaining green-yellow solid, and the red mixture was stirred at room temperature for 39 h. The mixture was poured into a mixture of ice (60 g) and pH 7.4 phosphate buffer (60 mL).

The precipitate was removed by filtration, washed with water, and taken up in EtOAc (60 mL). This solution was washed with water (3×50 mL), dried (brine, Na$_2$SO$_4$), and evaporated. The remaining oil was triturated with Et$_2$O. The precipitate was collected by filtration, purified by flash column chromatography (silica gel, EtOAc), and triturated with Et$_2$O to give 17a (0.38 g, 44%) as a pale yellow solid: mp 182–184° C.; $^1$H NMR (CDCl$_3$) δ 9.59 (s, 1 H), 8.84 (dd, J=4.2, 1.6 Hz, 1 H), 8.37 (s, 1 H), 7.95 (dd, J=8.5, 1.6 Hz, 1 H), 7.58 (br d, J=7.2 Hz, 2 H), 7.38 (dd, J=8.5, 4.2 Hz, 1 H), 7.36 (dd, J=7.3, 7.2 Hz, 2 H), 7.30 (t, J=7.3 Hz, 1 H), 6.93 (d, J=2.2 Hz, 1 H), 6.84 (s, 1 H), 5.48, 5.42 (2×d, J=12.5 Hz, 1 H each), 4.69 (dd, J=10.8, 1.9 Hz, 1 H), 4.57 (dd, J=10.8, 8.5 Hz, 1 H), 4.06, 3.93, 3.90 (3×s, 3 H each), 4.02 (dddd, J=10.3, 8.5, 3.2, 1.9 Hz, 1 H), 3.83 (dd, J=11.4, 3.2 Hz, 1 H), 3.42 (dd, J=11.4, 10.3 Hz, 1 H); $^{13}$C NMR (CDCl$_3$) δ 160.5, 155.3, 147.8, 150.2, 142.3, 140.6, 138.8, 138.2, 129.5, 125.1, 123.5, 136.4, 130.4, 128.6, 128.0, 127.7, 125.6, 122.3, 115.3, 106.7, 102.3, 97.6, 70.8, 61.4, 61.1, 56.2, 55.1, 45.9, 42.5. $C_{31}H_{28}ClN_3O_5$ requires M+H 558.1796, 560.1766. Found (FAB) 558.1770, 560.1786. Anal. Calcd for $C_{31}H_{28}ClN_3O_5$: C, 66.72; H, 5.06; N, 7.53. Found: C, 66.96; H, 5.36; N, 7.50.

1-(Chloromethyl)-5-hydroxy-3-[(5,6,7-trimethoxyindol-2-yl)carbonyl]-2,3-dihydro-1H-pyrrolo[3,2-f]quinoline (18a). Method 1. THF (10 mL) then 25% aqueous NH$_4$HCO$_3$ (1.1 mL) were added to a cooled (ice-water) mixture of 17a (0.25 g, 0.45 mmol) and 10% Pd/C (0.13 g) under nitrogen. The mixture was stirred at 0° C. for 7.5 h, and was then filtered through Celite. The Celite was washed with a solution of concentrated HCl (2 mL) and MeOH (40 mL) and then with CH$_2$Cl$_2$—MeOH (3:1, 40 mL). The combined filtrates were diluted with water (40 mL) and CH$_2$Cl$_2$ (30 mL) and neutralized with pH 7.4 phosphate buffer. The lower layer was separated then diluted with MeOH (20 mL) and warmed to dissolve the suspended solid. The aqueous phase was extracted with CH$_2$Cl$_2$ (2×20 mL). The extracts were combined, washed with water (100 mL), dried (Na$_2$SO$_4$), and concentrated to a volume of 20 mL. The concentrate was diluted with MeOH (20 mL) and was concentrated to a volume of 10 mL. The precipitate was removed by filtration and washed with MeOH to give 18a (0.14 g, 66%) as a pale yellow microcrystalline solid: mp>230° C.; $^1$H NMR [(CD$_3$)

$_2$SO]δ 11.50 (d, J=2.1 Hz, 1 H), 10.03 (br s, 1 H), 8.76 (dd, J=4.1, 1.3 Hz, 1 H), 8.40 (dd, J=8.4, 1.3 Hz, 1 H), 7.97 (s, 1 H), 7.56 (dd, J=8.4, 4.1 Hz, 1 H), 7.09 (d, J=2.1 Hz, 1 H), 6.97 (s, 1 H), 4.77 (dd, J=11.0, 9.3 Hz, 1 H), 4.48 (dd, J=11.0, 2.0 Hz, 1 H), 4.25 (dddd, J=9.3, 3.9, 3.3, 2.0 Hz, 1 H), 4.03 (dd, J=10.6, 3.3 Hz, 1 H), 3.93, 3.82, 3.80 (3×s, 3 H each), 3.89 (dd, J=10.6, 3.9 Hz, 1 H); $^{13}$C NMR ((CD$_3$)$_2$SO) δ 160.3, 153.9, 146.3, 149.1, 142.7, 139.9, 139.0, 136.0, 130.7, 125.4, 124.8, 123.1, 131.6, 122.4, 114.6, 106.2, 102.8, 98.0, 61.0, 60.9, 55.9, 55.0, 47.6, 40.5. Anal. Calcd for C$_{24}$H$_{22}$ClN$_3$O$_5$: C, 61.61; H, 4.74; Cl, 7.58; N, 8.98. Found: C, 61.50; H, 4.98; N, 8.84.

Compound 18a by Method 2. A solution of 16 (0.14 g, 0.43 mmol) in dioxane (9 mL) was saturated with HCl, allowed to stand for 1 h, and evaporated. 5,6,7-Trimethoxyindole-2-carboxylic acid (0.11 g, 0.43 mmol), EDCI (0.25 g, 1.28 mmol) and DMA (5 mL) were added to the remaining yellow solid, and the red mixture was stirred at room temperature for 22 h. The mixture was poured into a mixture of ice (20 g) and pH 7.4 phosphate buffer (20 mL). The precipitate was removed by filtration, washed with water, and taken up in CH$_2$Cl$_2$—MeOH (2:1, 30 mL). The CH$_2$Cl$_2$ was boiled off, the remaining mixture was cooled in ice, and the precipitate was removed by filtration to give 18a (18 mg, 9%) identical to the material prepared above.

Similarly were prepared:

1-(Chloromethyl)-3-({5-[2-(dimethylamino)ethoxyl]-5-hydroxyindol-2-yl}carbonyl)-2,3-dihydro-1H-pyrrolo[3,2-f]quinoline (18b).

A suspension of 14 (0.20 g, 0.47 mmol) in cooled (0° C.) dioxane (5 mL) was saturated with HCl, allowed to warm to r.t. over 2 h and evaporated. 5-[2-(Dimethylamino)ethoxy]-1-H-indole-2-carboxylic acid hydrochloride (0.13 g, 0.47 mmol) [Milbank et al., J. Med. Chem., 1999, 42, 649], EDCI (0.27 g, 1.42 mmol) and DMA (3 mL) were added to the remaining yellow solid, and the red mixture was stirred at r.t. for 20 h. The mixture was partitioned between EtOAc and 5% NaHCO$_3$ solution. The aqueous layer was extracted with EtOAc (×3). The EtOAc extracts were dried (brine, Na$_2$SO$_4$). Flash chromatography (Alumina, EtOAc/MeOH; 49:1, then 9:1) gave 2-[(2-{[5-(benzyloxy)-1-(chloromethyl)-1,2-dihydro-3H-pyrrolo[3,2-f]quinolin-3-yl]carbonyl}-1H-indol-5-yl)oxy]-N,N-dimethylethanamine (17b) (0.22 g, 84%) as a yellow solid: mp 176–179° C.; $^1$H NMR [(CD$_3$)$_2$SO]δ 11.68 (s, 1 H), 8.79 (dd, J=4.1, 1.5 Hz, 1 H), 8.41 (dd, J=8.6, 1.5 Hz, 1 H), 8.29 (s, 1 H), 7.56 (m, 3 H), 7.40 (m, 4 H), 7.17 (d, J=2.3 Hz, 1 H ), 7.11 (d, J=1.5 Hz, 1 H), 6.92 (dd, J=9.0, 2.4 Hz, 1 H), 5.32 (s, 2 H), 4.82 (dd, J=10.7, 9.6 Hz, 1 H), 4.58 (dd, J=10.9, 2.1 Hz, 1 H), 4.32 (m, 1 H), 4.05 (t, J=5.7 Hz, 2 H), 4.04 (m, 1 H), 3.93 (dd, J=11.2, 6.9 Hz, 1 H), 2.65 (t, J=5.8 Hz, 2 H), 2.23 (s, 6H); $^{13}$C NMR [(CD$_3$)$_2$SO]δ 160.3, 154.5, 153.0, 147.3, 142.3, 137.4, 136.7, 131.6, 131.3, 130.6,128.4, 127.9, 127.7, 127.4, 125.1, 122.4, 116.2, 116.0, 113.1, 105.5, 103.1, 102.0, 70.0, 66.9, 66.2, 57.8, 54.9, 47.7, 45.5, 40.7.

THF (8 mL) then HCO$_2$N$_4$ (0.23 g, 3.6 mmol) in H$_2$O (1 mL) were added to cooled (0° C.) mixture of 17b (0.20 g 0.36 mmol) and 10% Pd/C (0.1 g) under N$_2$. The mixture was stirred at 0° C. for 14 h, and was then filtered through Celite. The Celite was washed with CH$_2$Cl$_2$/H$_2$O. The aqueous layer was extracted with CH$_2$Cl$_2$(×3). The CH$_2$Cl$_2$ extracts were dried (brine, Na$_2$SO$_4$) and passed through a short plug of silica gel to give 18b (0.16 g, 93%) as a yellow solid: mp 209–215° C.; $^1$H NMR [(CD$_3$)$_2$SO]δ 11.66 (s, 1 H), 10.02 (bs, 1 H), 8.76 (dd, J=4.1, 1.4, 1 H), 8.41 (dd, J=8.5, 1.3, 1 H), 8.07 (s, 1 H), 7.56 (dd, J=8.5, 4.1, 1 H), 7.40 (d, J=8.9, 1 H), 7.17 (d, J=2.2, 1 H), 7.11 (d, J=1.2, 1 H), 6.93 (dd, J=8.9, 2.3, 1 H), 4.82 (dd, J=10.7, 9.6, 1 H), 4.57 (dd, J=11.0, 2.1, 1 H), 4.29 (m, 1 H), 4.06 (t, J=5.9, 2 H), 4.04 (m, 1 H), 3.91 (dd, J=11.1, 7.2, 1 H), 2.64 (t, J=5.8, 2 H), 2.28 (s, 6 H); $^{13}$C NMR [(CD$_3$)$_2$SO]δ 160.3, 153.9, 153.0, 146.4, 142.8, 136.1, 131.6, 130.7, 127.4, 124.8, 124.7, 122.5, 116.0, 114.6, 113.1, 105.5, 103.1, 103.0, 66.1, 57.8, 54.9, 47.7, 45.5, 40.7.

1-Chloromethyl)-3-((2E)-3-{4-[2-(dimethylamino)ethoxy]phenyl}-2-propenoyl)-5-hydroxy-2,3-dihydro-1H-pyrrolo[3,2-f]quinoline (18c).

A suspension of 14 (0.20 g, 0.47 mmol) in cooled (0° C.) dioxane (5 mL) was saturated with HCl, allowed to warm to r.t. over 1 h and evaporated. (E)-4-[2-(Dimethylamino)ethoxy]cinnamic acid hydrochloride (0.13 g, 0.47 mmol) [Atwell et al., J. Med. Chem., 1999, 42, 3400], EDCI (0.27 g, 1.42 mmol) and DMA (3 mL) were added to the remaining yellow solid, and the red mixture was stirred at r.t. for 30 h. The mixture was partitioned between CH$_2$Cl$_2$ and 5% NaHCO$_3$ solution. The aqueous layer was extracted with CH$_2$Cl$_2$ (×3). The CH$_2$Cl$_2$ extracts were dried (brine, Na$_2$SO$_4$). Flash chromatography (Alumina, EtOAc/MeOH; 49:1, then 24:1) gave 2-(4-{(1E)-3-[5-(benzyloxy)-1-(chloromethyl)-1,2-dihydro-3H-pyrrolo[3,2-f]quinolin-3-yl]-3-oxo-1-propenyl}phenoxy)-N,N-dimethylethanamine (17c) (0.18 g, 70%) as a yellow solid: mp 172–175° C.; $^1$H NMR [(CD$_3$)$_2$SO]δ 8.76 (dd, J=4.1, 1.4, 1 H), 8.47 (bs, 1 H), 8.35 (dd, J=8.5, 1.4, 1 H), 7.76 (d, J=8.7, 2 H), 7.67 (d, J=15.3, 1 H), 7.58 (d, J=7.3, 2 H), 7.54 (dd, J=8.5, 4.1, 1 H), 7.44 (t, J=7.2, 2 H), 7.37 (t, J=7.2, 1 H), 7.08 (d, J=15.3, 1 H), 7.02 (d, J=8.7, 2 H), 5.31 (s, 2 H), 4.55 (dd, J=10.7, 9.5, 1 H), 4.44 (dd, J=10.9, 2.5, 1 H), 4.30 (m, 1 H), 4.11 (t, J=5.8, 2 H), 3.99 (dd, J=11.0, 3.0, 1 H), 3.91 (dd, J=11.2, 7.2, 1 H), 2.64 (t, J=5.7, 2 H), 2.23 (s, 6 H); $^{13}$C NMR [(CD$_3$)$_2$SO]δ 164.1, 160.1, 154.6, 147.1, 142.6, 142.2, 137.2, 136.7, 131.1, 130.1, 128.3, 127.83, 127 78, 127.3, 125.1, 122.3, 116.9, 115.7, 114.7, 101.6, 70.0, 65.9, 57.5, 52.9, 47.8, 45.4, 40.1.

A solution of 17c (0.56 g, 1.03 mmol) was dissolved in CF$_3$COOH (15 mL) and refluxed for 48 h. CF$_3$COOH was evaporated and the residue was partitioned between CH$_2$Cl$_2$ and cold 5% NaHCO$_3$ solution. The aqueous layer was extracted with CH$_2$Cl$_2$ (×3). The CH$_2$Cl$_2$ extracts were dried (brine, Na$_2$SO$_4$). Flash chromatography (CH$_2$Cl$_2$/MeOH/NH$_3$; 95:5:trace) gave 18c (0.16 g, 34%) as a yellow solid: mp 174–180° C.; $^1$H NMR [(CD$_3$)$_2$SO]δ 9.96 (bs, 1 H), 8.73 (dd, J=4.0, 1.3, 1 H), 8.36 (dd, J=8.4, 1.3, 1 H), 8.18 (bs, 1 H), 7.77 (d, J=8.7, 2 H), 7.66 (d, J=15.2, 1 H), 7.54 (dd, J=8.5, 4.1, 1 H), 7.08 (d, J=15.4, 1 H), 7.02 (d, J=8.7, 2 H), 4.54 (dd, J=10.7, 9.5, 1 H), 4.44 (dd, J=11.0, 2.5, 1 H), 4.28 (m, 1 H), 4.11 (t, J=5.7, 2 H), 4.00 (dd, J=11.0, 3.1, 1 H), 3.88 (dd, J=11.0, 7.4, 1 H), 2.64 (t, J=5.8, 2 H), 2.22 (s, 6 H).

1-(Chloromethyl)-3-[(5-methoxyindol-2-yl)carbonyl]-5-hydroxy-2,3-dihydro-1H-pyrrolo[3,2-f]quinoline (18d).

A suspension of 14 (0.10 g, 0.24 mmol) in dioxane (15 mL) was saturated with HCl, stirred at r.t. for 5 h and evaporated. 5-Methoxy-1-H-indole-2-carboxylic acid (0.054 g, 0.28 mmol), EDCI (0.23 g, 1.17 mmol) and DMA (5 mL) were added to the remaining yellow solid, and the red mixture was stirred at r.t. for 52 h. The mixture was partitioned between CH$_2$Cl$_2$ and cold 5% KHCO$_3$ solution. The aqueous layer was extracted with CH$_2$Cl$_2$ (×3). The CH$_2$Cl$_2$ extracts were dried (brine, Na$_2$SO$_4$). Flash chromatography (EtOAc/petroleum ether, 7:3) gave 5-(benzyloxy)-1-(chloromethyl)-3-[(5-methoxy-1H-indol-2-yl)carbonyl]-2,3-dihydro-1H-pyrrolo[3,2-f]quinoline (17d) (0.11 g, 98%) as a yellow solid: mp 186–189° C.; $^1$H NMR (CDCl$_3$) δ 9.55 (s, 1 H), 8.88 (dd, J=4.2, 1.7, 1 H), 8.37 (s, 1 H), 7.99 (dd, J=8.3, 1.6, 1 H), 7.56 (d, J=7.3, 2 H), 7.42 (dd, J=8.3, 4.1, 1 H), 7.33 (m, 4 H), 7.10 (d, J=2.3, 1 H), 6.99 (m, 2 H), 5.48 (d, J=12.5, 1 H), 5.42 (d, J=12.6, 1 H), 4.74 (dd, J=10.9, 2.0, 1 H), 4.61 (dd, J=10.6, 8.7, 1 H), 4.05 (m, 1 H), 3.85 (s, 3 H), 3.84 (dd, J=11.2, 4.1, 1 H), 3.45 (dd, J=11.0, 10.5, 1 H); $^{13}$C NMR (CDCl$_3$) δ 160.7, 155.4, 154.7, 147.9, 142.4, 138.4, 136.4, 131.4, 130.5, 130.2, 128.6, 128.2, 128.0, 127.7, 125.2, 122.4, 117.0, 115.4, 112.7, 106.2, 102.5, 102.4, 70.9, 55.7, 55.2, 45.9, 42.6.

THF (6 mL) then HCO$_2$NH$_4$ (0.14 g, 2.21 mmol) in H$_2$O (0.7 mL) were added to cooled (0° C.) mixture of 17d (0.11 g, 0.22 mmol) and 10% Pd/C (0.05 g) under N$_2$. The mixture was stirred at 0° C. for 5 h, and was then filtered through Celite. The Celite was washed with CH$_2$Cl$_2$/H$_2$O. The aqueous layer was extracted with CH$_2$Cl$_2$ (×3). The CH$_2$Cl$_2$ extracts were dried (brine, Na$_2$SO$_4$) and CH$_2$Cl$_2$ evaporated. Precipitation from CH$_2$Cl$_2$/MeOH gave 18d (0.077 g, 89%) as a grey solid: mp 224–227° C.; $^1$H NMR [(CD$_3$)$_2$SO]δ 11.66 (s, 1 H), 10.02 (bs, 1 H), 8.77 (dd, J=4.1, 1.3, 1 H), 8.41 (dd, J=8.4, 1.4, 1 H), 8.07 (s, 1 H), 7.57 (dd, J=8.4, 4.1, 1 H), 7.40 (d, J=9.0, 1 H), 7.16 (d, J=2.4, 1 H), 7.12 (d, J=1.6, 1 H), 6.92 (dd, J=8.9, 2.3, 1 H), 4.82 (dd, J=10.8, 9.4, 1 H), 4.57 (dd, J=11.0, 2.3, 1 H), 4.30 (m, 1 H), 4.04 (dd, J=11.1, 3.3, 1 H), 3.91 (dd; J=11.1, 7.2, 1 H), 3.78 (s, 3 H).

1-(Chloromethyl)-3-[(2E)-3-(4-methoxyphenyl)-2-propenoyl]-5-hydroxy-2,3-dihydro-1H-pyrrolo[3,2-f]quinoline (18e).

A suspension of 16 (0.10 g, 0.30 mmol) in dioxane (5 mL) was saturated with HCl, stirred at r.t. over 5 h and evaporated. 4-Methoxycinnamic acid (predominantly trans) (0.064 g, 0.36 mmol), EDCI (0.29 g, 1.50 mmol) and DMA (3 mL) were added to the remaining yellow solid, and the red mixture was stirred at r.t. for 3 h. The mixture was partitioned between CH$_2$Cl$_2$ and cold 5% KHCO$_3$ solution. The aqueous layer was extracted with CH$_2$Cl$_2$ (×3). The CH$_2$Cl$_2$ extracts were dried (brine, Na$_2$SO$_4$). Flash chromatography (CH$_2$Cl$_2$/MeOH; 93:7) followed by recrystallisation (CH$_2$Cl$_2$/Et$_2$O) gave 18e (0.02 g, 17%) as a yellow solid: mp 208–211° C.; $^1$H NMR [(CD$_3$)$_2$SO]δ 9.96 (bs, 1 H), 8.73 (d, J=3.3, 1 H), 8.35 (d, J=7.7, 1 H), 8.18 (bs, 1 H), 7.78 (d, J=8.7, 2 H), 7.67 (d, J=15.3, 1 H), 7.54 (dd, J=8.5, 4.1, 1 H), 7.08 (d, J=15.4, 1 H), 7.01 (d, J=8.7, 2 H), 4.54 (dd, J=10.3, 9.5, 1 H), 4.45 (m, 1 H), 4.27 (m, 1 H), 3.99 (dd, J=11.1, 3.2, 1 H), 3.88 (dd, J=11.1, 7.3, 1 H), 3.82 (s, 3 H). C$_{22}$H$_{20}$ClN$_2$O$_3$ requires M+H 395.1163, 397.1133. Found (FAB) 395.1161, 397.1169.

1-(Chloromethyl)-3-[(2E)-3-(3-hydroxy-4methoxyphenyl)-2-propenoyl]-5-hydroxy-2,3-dihydro-1H-pyrrolo[3,2-f]quinoline (18f).

A suspension of 16 (0.10 g, 0.30 mmol) in dioxane (5 mL) was saturated with HCl, stirred at r.t. over 5 h and evaporated. 3-Hydroxy-4-methoxycinnamic acid (predominantly trans) (0.070 g, 0.36 mmol), EDCI (0.29 g, 1.50 mmol) and DMA (3 mL) were added to the remaining yellow solid, and the red mixture was stirred at r.t. for 3 h. The mixture was partitioned between CH$_2$Cl$_2$ and cold 5% KHCO$_3$ solution. The aqueous layer was extracted with CH$_2$Cl$_2$ (×3). The CH$_2$Cl$_2$ extracts were dried (brine, Na$_2$SO$_4$). Flash chromatography (CH$_2$Cl$_2$/MeOH; 93:7) followed by recrystallisation (CH$_2$Cl$_2$/Et$_2$O) gave 18f (0.01 g, 8%) as a yellow solid: mp 215–218° C.; $^1$H NMR [(CD$_3$)$_2$SO]δ 9.96 (bs, 1 H), 9.13 (s, 1 H), 8.73 (dd, J=4.1, 1.4, 1 H), 8.36 (dd, J=8.5, 1.4, 1 H), 8.17 (bs, 1 H), 7.57 (d, J=15.3, 1 H), 7.54 (dd, J=8.5, 4.1, 1 H), 7.25 (d, J=2.0, 1 H), 7.20 (dd, J=8.4, 2.0, 1 H), 6.99 (d, J=8.1, 1 H), 6.96 (d, J=15.0, 1 H), 4.54 (dd, J=10.5, 9.4, 1 H), 4.44 (m, 1 H), 4.00 (dd, J=11.2, 3.3, 1 H),3.88 (dd, J=11.1, 7.5, 1 H), 3.83 (s, 3H). C$_{22}$H$_{19}$$^{35}$ClN$_2$O$_4$ requires M+H 411.1112. Found (FAB) 411.1127.

Example B

Preparation of 5-amino-1-(chloromethyl)-3-[(5,6,7-trimethoxyindol-2-yl)carbonyl]-2,3-dihydro-1H-pyrrolo[3,2-f]quinoline 27 by the Method of Scheme 4

8-Nitroquinoline-6-carboxylic acid (19). This was prepared by the reported method [Jung et al., Eur. Pat. Appln. EP 581500 (1994); Chem Abstr, 1994, 122, 205125] in 41% yield: mp (EtOAc) 258–263° C.; $^1$H NMR [(CD$_3$)$_2$SO] δ 13.80 (v br, 1 H), 9.16 (dd, J=4.3, 1.7 Hz, 1 H), 8.96 (d, J=1.7 Hz, 1 H), 8.80 (dd, J=8.4, 1.6 Hz, 1 H), 8.63 (d, J=1.7 Hz, 1 H), 7.84 (dd, J=8.4, 4.2 Hz, 1 H).

6-(tert.-Butyloxycarbonylamino)-8-nitroquinoline (20)

A mixture of 19 (4.82 g, 22.1 mmol), DPPA (6.99 g, 25.4 mmol) and Et$_3$N (3.69 mL, 26.5 mmol) in anhydrous t-BuOH (60 mL) was heated at reflux under N$_2$ for 8 h. The mixture was concentrated under reduced pressure, and the residue was partitioned between CH$_2$Cl$_2$ and 10% aqueous KHCO$_3$. The organic phase was washed with 10% aqueous KHCO$_3$, dried (Na$_2$SO$_4$) and concentrated under reduced pressure, then chromatographed on silica gel. Elution with CH$_2$Cl$_2$/EtOAc (17:3), followed by sequential crystallisation from MeOH/H$_2$O and CH$_2$Cl$_2$/petroleum ether gave 20 (3.82 g, 60%): mp 134–135° C.; $^1$H NMR [(CD$_3$)$_2$SO]δ 10.09 (s, 1 H), 8.87 (dd, J=4.1, 1.5 Hz, 1 H), 8.47 (dd, J=8.5, 1.6 Hz, 1 H), 8.33 (d, J=1.9 Hz, 1 H), 8.25 (d, J=2.2 Hz, 1 H), 7.65 ,m(dd, J=2.2 Hz, 1 H), 7.65 (dd, J=8.5, 4.2 Hz, 1 H), 1.53 (s, 9 H). Anal. Calcd. for C$_{14}$H$_{15}$N$_3$O$_4$: C, 58.12; H, 5.23; N, 14.53. Found: C, 58.39; H, 5.21; N, 14.65%.

8-Amino-6-(tert.-butyloxycarbonylamino)quinoline (21) A solution of 20 (3.30 g, 11.4 mmol) in MeOH (50 mL) was hydrogenated over 10% Pd/C at 50 psi for 3 h. The resulting crude product was filtered through a column of silica gel in EtOPAc to give 21 (2.71 g, 92%): mp (i-Pr$_2$O/petroleum ether) 131–132° C.; $^1$H NMR [(CD$_3$)$_2$SO]δ 9.39 (s, 1 H), 8.54 (dd, J=4.1, 1.6 Hz, 1 H), 8.01 (dd, J=8.3, 1.5 Hz, 1 H), 7.36 (dd, J=8.3, 4.1 Hz, 1 H), 7.24 (d, J=2.0 Hz, 1 H), 6.97 (d, J=2.1 Hz, 1 H), 5.90, 5.88 (2×s, 2 H, NH$_2$), 1.50 (s, 9 H). Anal. Calcd. for C$_{14}$H$_{17}$N$_3$O$_2$: C, 64.85; H, 6.61; N, 16.20. Found: C, 64.60; H, 6.77; N, 16.19%.

6-(tert.-Butyloxycarbonyl)-8-(1,3-dioxo-1,3-dihydro-2H-isoindol-2-yl)quinoline (22). A mixture of 21 (1.53 g, 5.90 mmol), phthalic anhydride (1.05 g, 7.09 mmol) and DMAP (36 mg, 5 mol %), in anhydrous pyridine (15 mL) was heated with stirring at 80° C. for 1 h. The mixture was concentrated under reduced pressure, then AcOH (10 mL) and Ac$_2$O (5 ml) were added and the mixture was stirred at 80° C. for a further 45 min. Concentration under reduced pressure, followed by addition of aqueous KHCO$_3$, gave a solid that was chromatographed on silica gel. Elution with CH$_2$Cl$_2$/EtOAc (4:1) gave a crude product that was crystallized from CH$_2$Cl$_2$/iPr$_2$O to give 22 (2.09 g): mp 217–218° C. (dec.); $^1$H NMR [(CD$_3$)$_2$SO]δ 10.00 (s, 1 H), 8.67 (d, J=3.2 Hz, 1 H), 8.39 (d, J=8.1 Hz, 1 H, H-4), 8.24 (s, 1 H), 8.80–7.89 (m, 5 H), 7.53 (dd, J=8.3, 4.1 Hz, 1 H), 1.53 (s, 9 H). Anal. Calcd. for C$_{22}$H$_{19}$N$_3$O$_4$: C, 67.85; H, 4.92; N, 10.79. Found: C, 67.87; H, 4.94; N, 10.87%.

5-Bromo-6-(teyt.-butyloxycarbonylamino)-8-(1,3-dioxo-1,3-dihydro-1H-isoindol-2-yl)quinoline (23). A mixture of 22 (1.79 g, 4.6 mmol) and NBS (0.98 g, 5.5 mmol) in anhydrous CH$_3$CN (50 mL) was stirred at reflux for 45 min, then concentrated under reduced pressure. The residue was dissolved in CH$_2$Cl$_2$, and the solution was washed with aqueous Na₂S₂O₅/NaHCO₃ and water (2x), dried (Na₂SO₄) and concentrated to dryness. The residue was chromatographed on silica gel, and elution with CH₂Cl₂/EtOAc (3:2) gave a crude product that was crystallized from EtOAc/iPr₂O to 23 (1.91 g, 89%): mp 210–211° C. (dec.); $^1$H NMR [(CD₃)₂SO]δ 9.19 (s, 1 H), 8.85 (dd, J=4.1, 1.4 Hz, 1 H), 8.65 (dd, J=8.6, 1.4 Hz, 1 H), 8.21 (s, 1 H), 8.07–7.92 (m, 4 H), 7.75 (dd, J=9.7, 4.2 Hz, 1 H), 1.50 (s, 9 H). Anal. Calcd. for $C_{22}H_{18}BrN_3O_4$: C, 56.42; H, 3.87; N, 8.98; Br, 17.06. Found: C, 56.49; H, 4.04; N, 8.86; Br, 16.87%.

5-Bromo-6-[N-(tert.-butyloxycarbonyl)-N-(3-chloro-2-propen-1-yl)amino]-8-(1,3-dioxo-1,3-dihydro-1H-isoindol-2-yl)quinotine (24). A solution of 23 (1.82 g, 3.89 mmol) in anhydrous DMF (20 mL) was treated at 0° C. under N₂ with NaH (0.20 g, 5.00 mmol, 60% in oil), and then stirred at 25° C. for 45 min. The mixture was then cooled to 0° C. and 1,3-dichloropropene (1.11 mL, 11.7 mmol) was added. The reaction mixture was warmed to 25° C., stirred for 4 h, and then diluted with CH₂Cl₂ (200 mL). The solution was washed with 10% aqueous KHCO₃ and water (2x), then dried (Na₂SO₄) and concentrated under high vacuum at 25° C. The residue was chromatographed on silica gel, eluting with CH₂Cl₂ then CH₂Cl₂/EtOAc (17:3) to give 24 (1.62 g, 77%) as a foam that was used directly; $^1$H NMR [(CD₃)₂SO] (mixture of rotamers of E and Z alkenes) δ 8.94 (d, J=4.0 Hz, 1 H), 8.73 (d, J=8.6 Hz, 1 H), 8.12–7.93 (m, 5 H), 7.80 (dd, J=8.6, 4.2 Hz, 1 H), 6.50–6.35 (m, 1 H), 6.21–6.02 (m, 1 H), 4.62–4.06 (m, 2 H), 1.51, 1.32 (2xs, 9 H). Anal. Calcd. for $C_{25}H_{21}BrClN_3O_4 \cdot 2H_2O$: C, 51.87; H, 4.35; N, 7.26. Found: C, 51.69; H, 3.87; N, 6.86%.

3-(tert.-Butyloxycarbonyl)-1-(chloromethyl)-5-(1,3-dioxo-1,3-dihydro-1H-isoindol-2-yl)-2,3-dihydro-1H-pyrrolo[3,2-f]quinoline (25). A mixture of 24 (1.96 g, 3.61 mmol) and catalytic AIBN (60 mg, 10 mol %) in anhydrous benzene (20 mL) was treated with Bu₃SnH (1.16 mL, 4.33 mmol) and heated at reflux under N₂ for 3 h. The reaction mixture was concentrated under reduced pressure and the residue was chromatographed on silica gel. Elution with CH₂Cl₂/EtOAc (17:3), followed by crystallisation from CH₂Cl₂/petroleum ether gave 25 (1.28 g, 76%): mp 163–165° C.; $^1$H NMR [(CD₃)₂SO]δ 8.70 (dd, J=4.1, 1.3 Hz, 1 H), 8.51 (dd, J=8.6, 1.4 Hz, 1 H), 8.45 (v br, 1 H), 8.06–7.90 (m, 4 H), 7.57 (dd, J=8.5, 4.1 Hz, 1 H), 4.44–4.34 (m, 1 H), 4.29 (t, J=10.5 Hz, 1 H), 4.19–3.99 (m, 3 H), 1.54 (s, 9 H). Anal. Calcd. for $C_{25}H_{22}ClN_3O_4$: C, 64.72; H, 4.78; N, 9.06. Found: C, 64.76; H, 4.92; N, 9.03%.

1-(Chloromethyl)-5-(1,3-dioxo-1,3-dihydro-1H-isoindol-2-yl)-3-[(5,6,7-trimethoxyindol-2-yl)carbonyl]-2,3-dihydro-1H-pyrrolo[3,2-f]quinoline (26). A solution of 25 (500 mg, 108 mmol) in dioxane at 10° C. was saturated with HCl gas, allowed to stand at 20° C. for 1 h, then evaporated to dryness under reduced pressure below 30° C. 5,6,7-Trimethoxyindole-2-carboxylic acid (298 mg, 1.19 mmol), EDCI (518 mg, 2.70 mmol) and anhydrous DMA (10 mL) were then added, and the mixture was stirred at 20° C. for 3 h. Addition of 10% aqueous KHCO₃ precipitated a solid that was chromatographed on silica gel. Elution with CH₂Cl₂/EtOAc (1:1), followed by crystallisation from EtOAc/iPr₂O, gave 1-(chloromethyl)-5-(phthalimido)-3-[(5,6,7-triethoxyindol-2-yl)carbonyl]-2,3-dihydro-1H-pyrrolo[3,2-f]quinoline 26 (392 mg, 6 1%): mp 189–191° C.; $^1$H NMR [(CD₃)₂SO]δ 11.54 (s, 1 H), 8.77 (dd, J=4.1, 1.4 Hz, 1 H), 8.75 (s, 1 H), 8.59 (dd, J=8.5, 1.4 Hz, 1 H), 8.08–7.92 (m, 4 H), 7.61 (dd, J=8.5, 4.2 Hz, 1 H), 7.14 (d, J=1.7 Hz, 1 H), 6.98 (s, 1 H), 4.89 (dd, J=10.8, 9.7 Hz, 1 H), 4.61 (dd, J=11.0, 2.3 Hz, 1 H), 4.55–4.44 (m, 1 H), 4.20–4.05 (m, 2 H), 3.94, 3.83, 3.81 (3xs, 3x3H). Anal. Calcd. for $C_{32}H_{25}ClN_4O_6$: C, 64.37; H, 4.22; N, 9.39. Found: C, 64.04; H, 4.28; N, 9.29%.

5-Amino-1-(chloromethyl)-3-[(5,6,7-trimethoxyindol-2-yl)carbonyl]-2,3-dihydro-1H-pyrrolo[3,2-f]quinoline (27). A solution of 26 (160 mg, 0.27 mmol) in CH₂Cl₂ (6 mL) was diluted with EtOAc (8 mL) and treated immediately with hydrazine monohydrate (155 µL, 3.19 mmol). The reaction mixture was stirred at 25° C. for 2 h, then diluted with CH₂Cl₂ (40 mL), washed with 10% aqueous Na₂CO₃ (2x) and saturated aqueous NaCl (2x), dried (Na₂SO₄) and concentrated under reduced pressure below 30° C. Chromatography on silica gel, eluting with CH₂Cl₂/EtOAc (1:1) gave 27 (81 mg, 65%): mp 225–227° C.; $^1$H NMR [(CD₃)₂SO]δ 11.44 (s, 1 H), 8.63 (dd, J=4.1, 1.4 Hz, 1 H), 8.25 (dd, J=8.5, 1.4 Hz, 1 H), 7.82 (s, 1 H), 7.47 (dd, J=8.5, 4.1 Hz, 1 H), 7.05 (d, J=1.2 Hz, 1 H), 6.99 (s, 1 H), 6.18, 6.16 (2xs, 2 H), 4.70 (dd, J=10.8, 9.1 Hz, 1 H), 4.43 (dd, J=11.0, 1.8 Hz, 1 H), 4.16–4.08 (m, 1 H), 3.97 (dd, J=11.0, 3.3 Hz, 1 H), 3.94, 3.82, 3.80 (3xs, 3x3 H), 3.76 (dd, J=10.0, 7.8 Hz, 1 H). Anal. Calcd. for $C_{24}H_{23}ClN_4O_4$: C, 61.74; H, 4.96; N, 12.00. Found: C, 61.51; H, 5.04; N, 11.69%.

Example C

Preparation of 5-(2-aminoethylamino)-3-[(5,6,7-trimethoxyindol-2-yl)carbonyl]-1-(chloromethyl)-1,2-dihydro-3H-benz[e]indole Dihydrochloride 29 by the Method of Scheme 5

A mixture of 5-amino-1-(chloromethyl)-3-[5,6,7-trimethoxyindol-2-yl)carbonyl]-1,2-dihydro-3H-benz[e]indole 28 [Atwell et al., J. Org. Chem. 1998, 63, 9414] (252 mg, 0.54 mmol), N-(tert-butyloxycarbonyl)aminoacetaldehyde (430 mg, 2.70 mmol) TsOH (10 mg) and microwave-dried powdered A4 molecular sieves (3 g) in DMA (3 mL) and MeOH (0.5 mL) was stirred at 20° C. under N₂ with the exclusion of light for 48 h. NaBH₃CN (170 mg, 2.70 mmol) was added and the mixture was stirred for a further 4 h at 20° C., then poured into water. After prolonged cooling the resulting oily precipitate was collected and extracted with CH₂Cl₂. Following filtration the solution was washed with water, dried (Na₂SO₄) and then concentrated under reduced pressure below 30° C. The residue was chromatographed on silica gel, eluting with CH₂Cl₂/EtOAc (9:2), to provide material that was precipitated from a CH₂Cl₂ solution with petroleum ether at 20° C. to give 5-[2-(tert-butyloxycarbonylamino)ethylamino]-1-(chloromethyl)-3-[(5,6,7-trimethoxyindol-2-yl)carbonyl]-1,2-dihydro-3H-benz[e]indole (132 mg, 40%), mp 110–115° C. $^1$H NMR [(CD₃)₂SO]δ 11.45 (s, 1 H), 8.09 (d, J=8.5 Hz, 1 H), 7.79 (d, J=8.3 Hz, 1 H), 7.53–7.26 (underlying v br s, 1 H), 7.49 (t, J=7.7 Hz, 1 H), 7.33 (t, J=7.6 Hz, 1 H), 7.04 (s, 1 H), ca 7.07–7.00 (obscured signal, 1 H), 6.97 (s, 1 H), 6.28 (br s, 1 H), 4.68 (t, J=9.8 Hz, 1 H), 4.45 (dd, J=11.0, 1.4 Hz, 1 H), 4.17–4.07 (m, 1 H), 3.98 (dd, J=11.0, 3.0 Hz, 1 H), 3.92 (s, 3 H), 3.82 (s, 3 H), 3.80 (s, 3 H), 3.76 (dd, J=10.7, 8.0 Hz, 1 H), ca 3.3 (br s, obscured by H₂O signal but visible after D₂O exchange, 2 H), 3.18 (br s, 2 H), 1.39 (s, 9 H). Anal. Calcd. for $C_{32}H_{37}ClN_4O_6$: C, 63.1; H, 6.1; N, 9.2; Cl, 5.8. Found: C, 63.0; H, 6.1; N, 9.4; Cl, 5.7%.

A solution of the above compound (122 mg, 0.20 mmol) in dioxane (3 mL) was treated with HCl-saturated EtOAc (3 mL), and the mixture was stood at 20° C. for 1 h. Excess EtOAc was then added to complete separation of the product, which was collected and recrystalised from MeOH/EtOAc/petroleum ether/HCl to give 5-(2-aminoethylamino)-3-[(5,6,7-trimethoxyindol-2-yl)carbonyl]-1-

(chloromethyl)-1,2-dihydro-3H-benz[e]indole dihydrochloride 29 (86 mg, 74%), mp>200° C. $^1$H NMR [free base in (CD$_3$)SO]δ 11.46 (br s, 1 H), 8.17 (d, J=8.6 Hz, 1 H), 7.78 (d, J=8.2 Hz, 1 H), ca. 7.5–7.3 (underlying v br s, 1 H), 7.49 (t, J=7.6 Hz, 1 H), 7.32 (t, J=7.7 Hz, 1 H), 7.04 (s, 1 H), 6.97 (s, 1 H), 6.28 (t, J=5.0 Hz, 1 H), 4.67 (t, J=9.5 Hz, 1 H), 4.45 (dd, J=11.0, 1.3 Hz, 1 H), 4.19–4.07 (m, 1 H), 3.98 (dd, J=10.9, 3.0 Hz, 1 H), 3.92 (s, 3 H), 3.82 (s, 3 H), 3.80 (s, 3 H), 3.77 (dd, J=11.0, 8.2 Hz, 1 H), 3.12 (br s, 2 H), 2.84 (br s, 2 H). Anal. Calcd. for C$_{27}$H$_{29}$ClN$_4$O$_4$.2HCl.0.5H$_2$O: C, 54.9; H, 5.5; N, 9.5. Found: C, 55.1; H, 5.5; N, 9.1%.

Example D

Preparation of Ancillary Ligands 1,4,7,10-Tetraazacyclododecane-1,7-dipropanesulfonic acid tetrahydrochloride (32).

A solution of perhydro-3,6,9,12-tetraazacyclopenteno[1,3-f,g]acenaphthylene (30) (0.50 g, 2.58 mmol) [Weisman et al., Tetrahedron Lett., 21, 1980, 335] and 1,3-propanesultone (1.57 g, 12.9 mmol) in CH$_3$CN (20 mL) was stirred at 80° C. under N$_2$ for 72 h. The suspension was cooled to room temperature and the white precipitate was filtered and washed with excess CH$_3$CN to give 1,7-bis(3-sulfopropyl)-4,10-diaza-1,7-diazoniatetracyclo[5.5.2.0.$^{4,14}$0$^{10,13}$]tetradecane (31) (0.98 g, 86%): mp 279–281° C.; $^1$H NMR (D$_2$O) δ 4.49 (s, 2 H), 3.95 (m, 8 H), 3.82 (bd, J=13.3, 2 H), 3.60 (m, 4 H), 3.38 (bd, J=14.0, 2 H), 3.05 (m, 8 H), 239 (m, 2 H), 2.27 (m, 2 H); $^{13}$C NMR D$_2$O) δ 81.6, 64.2, 58.7, 57.6, 49.8, 49.0, 45.3, 21.4. C$_{16}$H$_{30}$N$_4$O$_6$S$_2$ requires M+H 439.1685. Found (FAB) 439.1686.

A mixture of 31 (0.50 g, 1.14 mmol) and hydrazine monohydrate (15 mL, 98%) were heated (100° C.) under N$_2$ for 48 h. Excess hydrazine was removed and the residue was dissolved in H$_2$O. Acidification with HCl gave a yellow solution. Evaporation of H$_2$O gave a brown solid (hygroscopic). Trituration with MeOH (×10) gave 32 (0.59 g, 91%) as a cream powder: mp 322–325° C.; $^1$H NMR (D$_2$O) δ 3.24 (m, 8 H), 2.94 (m, 12 H), 2.82 (m, 4 H), 1.95 (quintet, J=7.4, 4 H); $^{13}$C NMR (D$_2$O) δ 53.9, 51.7, 49.9, 45.1, 21.7.

1,4,7,10-Tetraazacyclododecane-1-butanesulfonic acid tetrahydrochloride (34).

A solution of 30 (0.50 g, 2.58 mmol) and 1,4-butanesulfone (1.75 g, 12.9 mmol) in CH$_3$CN (15 mL) was stirred at 60° C. under N$_2$ for 48 h. The suspension was cooled to room temperature and the white precipitate was filtered and washed with excess CH$_3$CN to give 4-decahydro-4a,6a,8a-triaza-2a-azoniacyclopenta[f,g]acenaphthylen-2a-yl-1-butanesulfonate (33) (0.82 g, 96%): mp 301–303° C.; $^1$H NMR (D$_2$O) δ 3.91 (m, 1 H), 3.91 (d, J=2.5, 1 H), 3.80 (m 3 H), 3.67 (m, 1 H), 3.58 (d, J=2.7, 1 H), 3.53 (m, 1 H), 3.43 (m, 1 H), 3.24 (m, 4 H), 3.00 (t, J=7.3, 2 H), 2.87 (m, 5 H), 2.50 (m, 2 H), 2.09 (m, 1 H), 1.98 (m, 1 H), 1.85 (m, 2 H); $^{13}$C NMR (D$_2$O) δ 86.5, 74.4, 64.8, 60.4, 59.6, 53.9, 52.5, 51.1, 50.9, 50.4, 50.3, 46.3, 24.2, 24.0. C$_{14}$H$_{26}$N$_2$O$_4$S requires M+H 331.1804. Found (FAB) 331.1806.

A mixture of 33 (0.30 g, 0.92 mmol) and hydrazine monohydrate (6 mL, 98%) was heated (80° C.) under N$_2$ for 36 h. Excess hydrazine was removed and the residue was dissolved in H$_2$O. Acidification with HCl gave a yellow solution. Evaporation of H$_2$O gave a brown solid (hygroscopic). Trituration with MeOH (×10) gave 34 (0.41 g, 97%) as a cream powder: mp 322–325° C.; $^1$H NMR (D$_2$O) δ 3.20 (m, 16 H), 2.95 (m, 4 H), 1.78 (m, 4 H); $^{13}$C NMR (D$_2$O) δ 56.2, 52.9, 52.1, 51.6, 46.4, 45.5, 44.9, 25.1, 24.4.

1,4,7,10-Tetraazacyclododecane-1,7-dipentanoic acid (36).

A solution of 30 (0.10 g, 0.52 mmol) and ethyl 4-iodobutyrate (0.79 g, 3.09 mmol) [Nudelman et al., Bioorg. Chem., 26, 1998, 157] in CH$_3$CN (5 mL) was stirred at 60° C. under N$_2$ for 6 days. A further portion of the iodide (0.26 g, 1.03 mmol) was added and the reaction was stirred at 60° C. under N$_2$ for 3 weeks. CH$_3$CN was removed and the residue was partitioned between CH$_2$Cl$_2$ and H$_2$O. The aqueous layer was extracted with CH$_2$Cl$_2$ (×6). H$_2$O was evaporated and the residue was solidified with CH$_3$CN/Et$_2$O followed by trituration with Et$_2$O (×4) to give 1,7-bis(ethoxycarbonylbutyl)-4,10-diaza-1,7-diazoniatetracyclo[5.5.2.0.$^{4,14}$0$^{10,13}$]tetradecane diiodide (35) (0.32 g, 87%): $^1$H NMR (D$_2$O) δ 4.46 (s, 2 H), 4.17 (q, J=7.2, 4 H), 3.92 (m, 6 H), 3.77 (m, 4 H), 3.59 (m, 2 H), 3.45 (td, J=12.8, 4.1, 2 H), 3.35 (bd, J=13.9, 2 H), 3.06 (m, 4 H), 2.48 (t, J=7.3, 4 H), 1.96 (m, 2 H), 1.85 (m, 2 H), 1.69 (quintet, J=7.3, 4 H), 1.25 (t, J=7.2, 6 H); $^{13}$C NMR (D$_2$O) δ 178.6, 81.2, 64.5, 64.4, 60.2, 57.9, 49.0, 45.3, 35.9, 24.8, 23.8, 16.1. C$_{24}$H$_{44}$I$_2$N$_4$O$_4$ requires M+H–I 579.2407. Found (FAB) 579.2410.

A mixture of 35 (0.05 g, 0.08 mmol) and 15% aqueous KOH (5 mL) was stirred at 70° C. under N$_2$ for 48 h. Water was evaporated and the residue was acidified to pH 2.5 with HCl. The mixture was loaded onto a DOWEX 50W-X8 cation exchange resin (H$^+$form). Elution with H$_2$O followed by 0.5M NH$_3$ gave 36 (0.03 g, 100%) as a colourless oil: $^1$H NMR (D$_2$O) δ 2.86 (m, 8 H), 2.68 (m, 8H), 2.53 (t, J=7.4, 4 H), 2.20 (q, J=7.0, 4 H), 1.55 (m, 4 H), 1.47 (m, 4 H); $^{13}$C NMR (D$_2$O) δ 183.1, 53.1, 49.1, 42.8, 37.1, 24.1, 23.8. C$_{18}$H$_{36}$N$_4$O$_4$ requires M+H 373.2815. Found (FAB) 373.2810.

Example E

Preparation of Metal Complexes

Preparation of Complex M1 of Table 1. [[Co(cyclen)18a]](ClO$_4$)$_2$].

[Co(cyclen)(NO$_2$)$_2$](NO$_2$) (38) [Collman and Schneider, Inorg. Chem. 1966, 5, 1380] (1.03 g, 2.79 mmol) was cautiously added with stirring to neat triflic acid (10 mL) cooled in an ice bath The solution was bubbled with N$_2$ to remove NO$_x$ gas and warmed briefly at 40–50° C. until reaction was complete. Dry Et$_2$O (250 mL was added slowly to the above cold solution (ice-bath) with vigorous stirring, and the resulting precipitate was filtered off, washed (4× dry Et$_2$O) and dried in a desiccator to give [Co(cyclen)(OTf)$_2$](OTf) (39) (1.95 g, 100%). Anal. Calcd. for C$_{11}$H$_{24}$CoF$_9$N$_4$O$_{11}$S$_3$: C, 18.49; H, 3.39; N, 7.85. Found: C, 18.43; H, 3.49; N, 7.84. HRMS FAB$^+$ [M–OTf]$^+$ calculated for: C$_{10}$H$_{20}$CoF$_6$N$_4$O$_6$S$_2$=529.00605. Found: 529.00406. (39) (90 mg, 0.132 mmol) was dissolved in dry CH$_3$CN (3 mL) and 18a (62 mg, 0.132 mmol) was added. To the stirred solution was added iPr$_2$NEt (25 mg, 1.5 equiv). This resulted in rapid darkening of the solution to a brown colour but with significant amounts of suspended yellow solid (unreacted/undissolved) 18a present. The mixture was stirred at room temperature for 11 days, during which time nearly all of the suspended solid disappeared. The small amount remaining was removed by filtration through a 0.45µ membrane filter and the filtrate made slightly acidic with dilute aqueous HClO$_4$. Excess 1 M NaClO$_4$ (aq) was added and the solution was extracted 4× with 5 mL CH$_3$NO$_2$. The combined extracts were evaporated to dryness, the residue resuspended in dry Et$_2$O (15 mL) and again evaporated to dryness (first on a Rotovapor, finally on a vacuum line) below 20° C., to give crude product as brown flakes of glassy material (103 mg, 86%). HRMS FAB [M–ClO$_4$]$^+$. This material was further purified on reverse-phase HPLC, and the pooled pure fractions were concentrated under reduced pressure, then combined with excess aqueous 1 M $NaClO_4$ and extracted 5× with $CH_2Cl_2$. The combined organic extracts were treated as above to give complex M1 as brownish flakes (~70 mg). HRMS $FAB^+$ $[M-2ClO_4-H]^+$ Calcd for $C_{32}H_{41}{}^{35}ClCoN_7O_5$; 697.21897. Found, 697.21327. Calcd for $C_{32}H_{41}{}^{37}ClCoN_7O_5$; 699.21602. Found, 699.21601.

Preparation of Complex M2 of Table 1. [[Co(cyclen)(18c)] $(ClO_4)_2$]

[Co(cyclen)(OTf)$_2$](OTf) (39) (0.087 g, 0.128 mmol) was dissolved in dry $CH_3CN$ (4 mL) and 18c (0.052 g, 0.115 mmol) was added. The mixture was stirred at room temperature for 8 h then cooled overnight at 5° C. A small amount of unreacted 18c was removed by filtration and the bright yellow solid washed with cold $CH_3CN$ and the washes added to the filtrate. This dark brown solution was reduced to ca. 2 mL by evaporation of solvent under reduced pressure and then chromatographed on a short (3.3×40 mm) flash silica gel column (0.32–0.60 μm). Elution started with MeOH($CH_3NO_2$) (5%) which was stepwise enriched with MeOH up to 15%. At this concentration the main band was eluted first followed closely by a small yellow brown band. A stationary red band remains at the top of the column. Removal of the solvent on a rotary evaporator then on a vacuum line to give M2 as a brown glassy residue (0.089 g, 79%). HRMS $FAB^+$ $[M-2OTf]^+$ Calcd. for $C_{32}H_{45}{}^{35}ClCoN_7O_3$ 681.26044. Found, 681.26064; for $^{37}Cl$=683.25749. Found, 683.26086.

Preparation of Complex M3 of Table 1. [[Co(cyclen)(18b)] $(ClO_4)_2$]

This was prepared as above from 39 (0.101 g, 0.149 mmol) and 18b (0.055 g, 0.118 mmol) to give, after flash chromatography on silica gel, M3 (0.078 g, 67%). HRMS $FAB^+$ $[M-2OTf]^+$ calculated for $C_{33}H_{44}{}^{35}ClCoN_8O_3$ 694.25569. Found=694.25305; for $^{37}Cl$=696.25274. Found=696.25401.

Preparation of Complex M4 of Table 1. [Cr(acac)$_2$(18a)].

Solid 18a (20 mg, 0.0427 mmol) was added to a solution of [Cr(acac)$_2$(H$_2$O)$_2$]ClO$_4$.2H$_2$O (mixture of cis and trans isomers; Ogino, et al., Inorg. Chem. 1988, 27, 986) (0.03 g, 0.071 mmol) in dry $CH_3CN$ (3 mL). The mixture was stirred and a solution of iPr$_2$NEt (6 mg, 0.0464 mmol) in $CH_3CN$ (0.5 mL) was added gradually over 1 h. The solution was warmed in an oil bath at 50° C. for 0.5 h, then stirred at ambient temperature for 2 weeks. During this period undissolved 18a gradually disappeared as the complexation reaction proceeded giving a clear red-brown solution. The solvent was removed under reduced pressure and the residue was dissolved in CHCl$^3$ (1.0 mL) and purified by flash chromatography on silica gel. Elution with a $CH_3CN/CHCl_3$ gradient from 0 to 50% $CH_3CN$ eluted a single yellow-brown band that trailed somewhat near the bottom of the column. The trailing material was eluted separately with 100% $CH_3CN$. A small amount of green irreversibly absorbed material was left at the top. The main band and tailing fraction were evaporated to dryness under reduced pressure to give yellow-brown powders of Cr(acac)$_2$(18a) (18 mg, 59% ) and (5 mg, 16%), respectively.

These two samples gave identical accurate mass spectral results; approximately equal amounts of both $[M]^+$ and $[M+H]^+$ ions observed with relative intensities consistent with one $^{35}Cl$ or $^{37}Cl$ per molecule. $FAB^+$-MS: $[M]^+$ calc. for $C_{34}H_{35}Cl^{52}CrN_3O_9$=716.14669. Found, $[M]^+$=716.14642. $[M+H]^+$ calc. for $C_{34}H_{36}{}^{37}Cl^{52}CrN_3O_9$=719.15157. Found, $[M+H]^+$=719.15122. Fragments corresponding to loss of acac ligand are observed, and the base peak corresponds to Cr(acac)$_2$. Analytical HPLC on an RP C-18 column using gradient elution starting from a 1:1 (v/v) mixture of 80% aqueous $CH_3CN$ and phosphate buffer (pH=7.4, 0.04 M) showed one major peak (96.7%) with a prominent UV absorption band at 339 nm. A small amount (0.45%) of uncomplexed 2 could be detected and its identity was confirmed by spiking. Because of the paramagnetic properties of the Cr(III) present in this complex, $^1H$ or $^{13}C$ resonances were not observed by NMR.

Preparation of Complex M5 of Table 1. [Co(Me$_2$dtc)$_2$(18a)]

[Co$_2$(Me$_2$dtc)$_5$]BF$_4$ (105 mg, 0.1303 mmol) [Hendrickson et al., J. Chem. Soc. Dalton Trans. 1975, 2182] was added to a suspension of 18a (46 mg, 0.0983 mmol) in 5% MeOH/$CH_2Cl_2$ (4 mL). iPr$_2$NEt (25 mg, 2 equiv) was added to stirred suspension in two portions with the second added one day after the first Stirring was continued at room temperature for 8 days, by which time very little suspended/unreacted 18a was evident, and the colour of the solution was the deep green of the co-product Co(Me$_2$dtc)$_3$. The solution was filtered and the filtrate evaporated under reduced pressure. The residue was taken up in $CH_2Cl_2$ (2 mL)

TABLE 2

| Compound | IC$_{50}$ (μM) | | | |
|---|---|---|---|---|
| | AA8 | UV4 | EMT6 | SKOV3 |
| Cytotoxic ligands | | | | |
| 29 | 0.0058 ± 0.0007 (2) | 0.0041 ± 0.0003 (2) | 0.0028 0.0004 (2) | 0.0062 |
| 18a | 0.00014 ± 0.000022 (7) | 0.00007 ± 0.000015 (6) | 0.000051 ± 0.000008 (5) | 0.00025 ± 0.000037 (8) |
| 27 | 0.0079 ± 0.002 (4) | 0.0029 ± 0.006 (4) | 0.0026 ± 0.0005 (4) | 0.012 ± 0.0023 (4) |
| 8-HQ | 2.07 ± 0.02 (3) | 2.16 ± 0.12 (3) | 3.92 ± 1.04 (2) | 4.07 ± 0.89 (2) |
| Ancillary ligands | | | | |
| TACN (VIIIc: $R^1$–$R^3$ = H) | 12700 ± 5770 (2) | 10100 ± 3930 (2) | 7710 ± 1010 (2) | 13500 ± 5480 (2) |
| Cyclen (IX; $Z^1$–$Z^4$ = (CH$_2$)$_2$; $R^1$–$R^4$ = H) | 13300 ± 2670 (2) | 13800 ± 2180 (2) | 9710 ± 2710 (3) | 11500 ± 4410 (2) |

TABLE 2-continued

| Compound | IC$_{50}$ (μM) | | | |
|---|---|---|---|---|
| | AA8 | UV4 | EMT6 | SKOV3 |
| Metal complexes | | | | |
| M1 | 0.0152 ± 0.0006 (2) | 0.0051 ± 0.0002 (2) | 0.0133 ± 0.0008 (2) | 0.015 ± 0.005 (3) |
| M4 | 0.088 ± 0.017 (3) | 0.03 ± 0.0018 (3) | 0.039 ± 0.011 (3) | 0.11 ± 0.018 (3) |
| M5 | 0.028 ± 0.003 (3) | 0.015 ± 0.001 (3) | 0.0095 ± 0.0012 (2) | 0.016 ± 0.003 (3) |
| M7 | 5,670 ± 45.0 (2) | 6,140 ± 820 (2) | 3,580 ± 95.4 (2) | 6,380 ± 1750 (3) |

The results of Table 2 show that the cytotoxic ligands 29, 18a and 27 are exceptionally cytotoxic. The results of Table 2 also show that metal complexation and chromatographed on a flash silica gel column. Elution began in CH$_2$Cl$_2$, and a large green band of Co(Me$_2$dtc)$_3$ was eluted. Stepwise enrichment with CH$_3$CN in increments of 10% was carried out until the product —[Co(Me$_2$dtc)$_2$(18a)] (M5) was eluted (with ca 50% CH$_3$CN/CH$_2$Cl$_2$). The main muddy yellow-green band was collected, and solvent was removed under reduced pressure to give the product as a brownish-green amorphous residue (48 mg, 63%). Analytical reverse-phase HPLC indicated no detectable free cytotoxic ligand 18a present.

Preparation of Complex M6 of Table 1. [[Cr(acac)$_2$(29)] ClO$_4$)]

A suspension of 29 (31 mg, 0.058 mmol) in CH$_3$OH (0.5 mL) was treated with a solution of NaOH (5 mg, 0.119 mmol) dissolved in CH$_3$OH (0.5 mL), and the neutralised solution was immediately added to a another containing a mixture of cis- and trans-[Cr(acac)$_2$(OH$_2$)$_2$]ClO$_4$.2H$_2$O (29 mg, 0.069 mmol) dissolved in CH$_3$CN (1.0 mL). The combined mixture was stirred at 50° C. for 15 min, cooled to room temperature and the solvent removed under reduced pressure. Chromatography on silica gel gave [Cr(acac)$_2$(29)] ClO$_4$ (M6) as a purple residue after drying under vacuum over silica gel desiccant. HRMS (FAB$^+$/NBA): Calculated [M$^+$] for C$_{37}$H$_{43}$N$_4$$^{35}$ClCrO$_8$, 758.21834. Found, 758.21745.

Preparation of Complex M7 of Table 1 [[Co(TACN)(8-HQ)(CN)]ClO$_4$]

Co(TACN)(NO$_2$)$_3$ was prepared from Na$_3$[Co(NO$_2$)$_6$], using the method of Wieghardt et al., Chem. Ber., 1979, 112, 2220–2230. This was then used to prepare [Co(TACN)(H$_2$O)$_3$](OTf)$_3$ (91% yield), essentially by the method of Galsboel et al., Acta Chem. Scand., 1996, 50, 567–570. [Co(TACN)(H$_2$O)$_3$](OTf)$_3$ (360 mg, 0.509 mmol) was dissolved in EtOH (9 mL) and 8-hydroxyquinoline (8-HQ) (73 mg, 0.6 mmol) added as a solid. Immediately a solution of Et$_3$N (62 mg) in EtOH (~4 mL) was added to the stirred solution, which was then warmed briefly to complete the coordination of 8-HQ to the cobalt centre. NaCN (150 mg, 4 equiv) was added portionwise, and the mixture was stirred for 24 hours. During the addition of NaCN and occasionally thereafter, the pH was adjusted to ca. 7 by addition of 0.1 M HClO$_4$. The red crystals and orange precipitate that formed were dissolved by dilution of the mixture with H$_2$O and the whole was loaded onto a Sephadex SP C-25 cation exchange column and thoroughly washed with H$_2$O. Elution with 0.05 M then 0.1 M NaClO$_4$ eluted the major band, and concentration of the eluate by evaporation under reduced pressure produced red-brown crystals of [Co(TACN)(8-HQ)(CN)] ClO$_4$ (M7) (117 mg, 51%) which were collected and washed with a little ice cold H$_2$O then 3× with Et$_2$O. Anal. Calcd for C$_{16}$H$_{21}$N$_5$ClO$_5$Co: C, 41.98; H, 4.62; N, 15.30; Cl, 7.74. Found; C, 41.99; H, 4.44; N, 15.28; Cl, 7.93.

Biological Activity

Selected complexes of Table 1, together with the uncomplexed cytotoxic ligands, were evaluated for cytotoxicity (measured as IC$_{50}$ values in μM following a 4 h aerobic drug exposure) in a panel of mammalian cell lines, and the results are given in Table 2. AA8 is a Chinese hamster ovary line, and the UV4 cell line is a repair-defective ERCC-1 mutant, sensitive to agents whose cytotoxicity is due to bulky DNA adducts. EMT6 is a murine mammary carcinoma line, and SKOV3 is a human ovarian cancer line.

Table 2. Shows the results of the biological activity for various cytotoxins and their metal complexes. IC$_{50}$ values are mean±sem (number of experiments in parentheses) for exposure of the indicated cell lines to compounds for 4 hr under aerobic conditions. results in considerable abrogation of cytotoxicity, indicating the utility of this approach in forming less toxic prodrugs of these compounds.

Complex M1 listed in Table 1 was also evaluated for its ability to release the cytotoxic ligands when exposed to ionising radiation in deoxygenated sodium formate buffer (measured as G values in μM/Gy for radiolytic reduction, where the G value for total reductants is 0.68 μM/Gy), and the results are given in Table 3.

TABLE 3

G values (μM/Gy) for release of cytotoxic ligand on radiolytic reduction in deoxygenated sodium formate buffer using 15 μM prodrug (complex M1).

| No | Metal | Cytotoxic ligand | Ancillary ligands | G value (μmol/Gy) |
|---|---|---|---|---|
| M1 | Co | 18a | Cyclen | 0.75 |

The results of Table 3 show that certain of these metal complexes also have the potential to cleanly release their cytotoxic ligand in good yield following exposure to ionising radiation. As a specific example, FIG. 1 shows the release of cytotoxin 18a (SN 26800) from complex M1 (SN 27892) when irradiated in 0.1M sodium formate buffer pH 7.0 under hypoxic conditions.

It is thought that the mechanism of activation of the prodrug is as illustrated in the following mechanistic pathway.

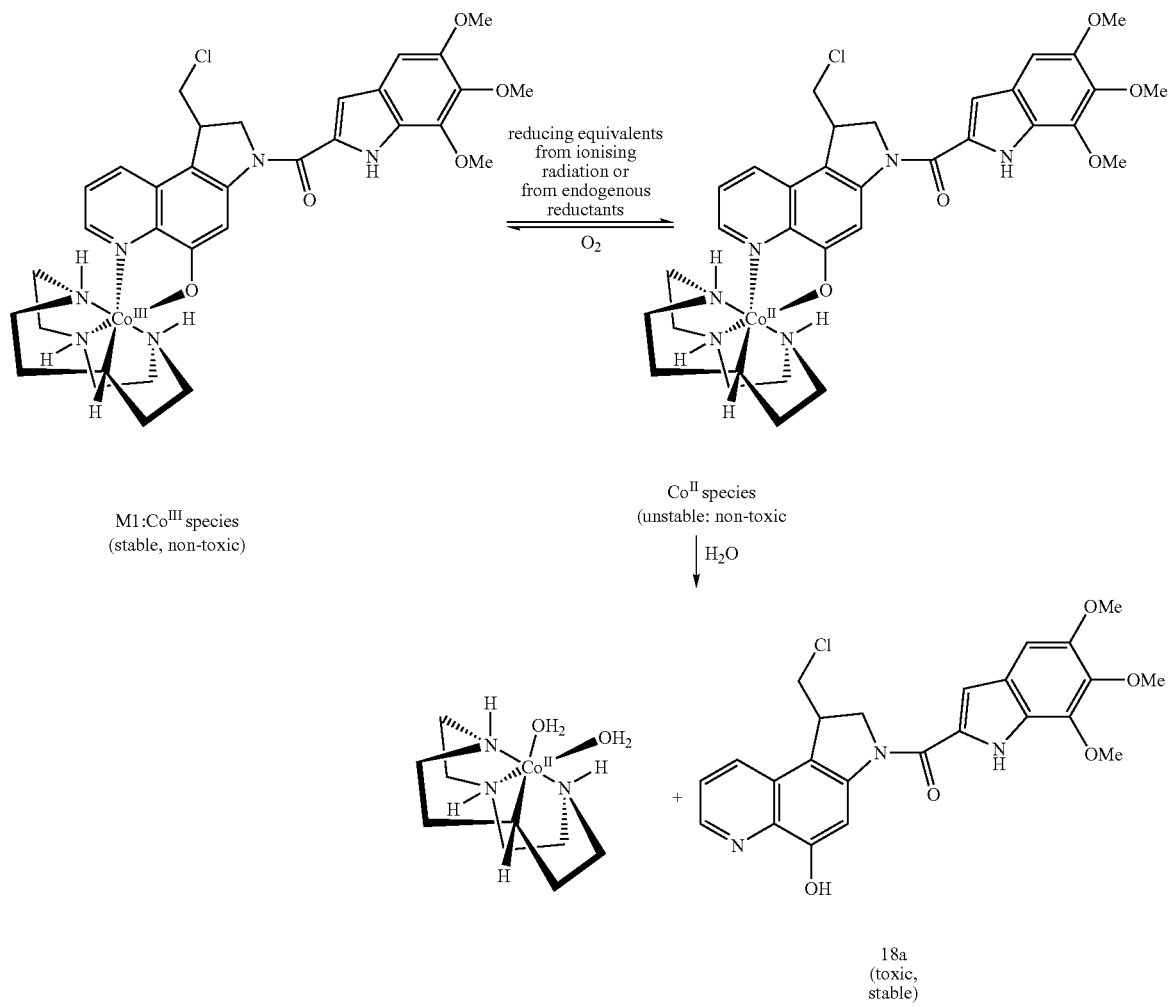

Figure 2:
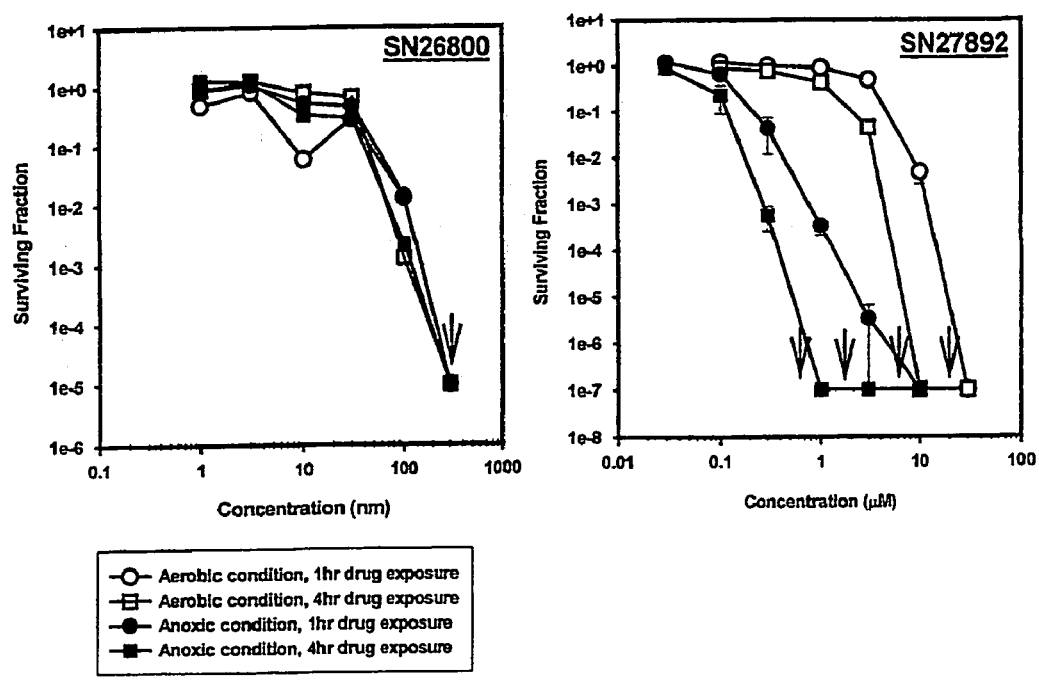
FIG. 2 shows graphically the hypoxic selectivity of metal complex M1 in HT29 cultures.

The metal complexes also show an ability to be activated by endogenous enzymes under hypoxia, as shown for metal complex M1 in Table 4 and FIG. 2. Table 4 and FIG. 2 also show that the corresponding cytotoxic ligand 18a is not activated by endogenous enzymes under hypoxic conditions. Thus the metal complexes have utility as hypoxia- as well as radiation-activated cytotoxins.

cytotoxicity ratio (HCR) is the average intra-experiment ratio of the $IC_{50}$s measured under oxic and hypoxic conditions.

Wherein the foregoing description reference has been made to reagents, or integers having known equivalents thereof, then those equivalents are herein incorporated as if individually set forth.

TABLE 4

Activation of metal complex M1 (but not the cytotoxin 18a) under hypoxia (4 h exposure).

| | $IC_{50}$ (nM) | | | | | | | | |
|---|---|---|---|---|---|---|---|---|---|
| | A549 wt/s | | | SKOV3 | | | WiDr-2 | | |
| | oxic | anoxic | HCR | oxic | anoxic | HCR | oxic | anoxic | HCR |
| 18a | 0.050 ± 0.016(3) | 0.050 ± 0.014(2) | 0.79 ± 0.35(2) | 0.25 ± 0.037(8) | 0.35 ± 0.093(2) | 0.61(1) | — | — | — |
| M1 | 5.60 ± 0.00(2) | 0.38 ± 0.16(2) | 18.0 ± 7.7(2) | 15.0 ± 5.0(3) | 1.7 ± 0.97(2) | 8.1(1) | 6.6 ± 0.45(2) | 1.7 ± 0.10(2) | 3.90 ± 0.50(2) |

In Table 4, A549wt/s is a wild-type human colon carcinoma cell line, SKOV3 is a human ovarian cancer cell line and WiDr-2 is a clonal cell line derived from the WiDr human colon carcinoma line. $IC_{50}$s (in μM are determined under both oxic and hypoxic conditions, and the hypoxic While this invention has been described with reference to certain embodiments and examples, it is to be appreciated that further modifications and variations may be made to embodiments and examples without departing from the spirit or scope of the invention.

What we claim is:

1. An 8-quinoline metal complex represented by Formula I

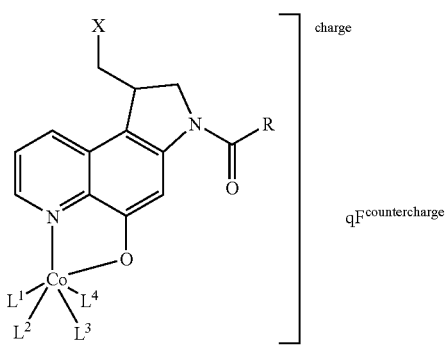

Formula I wherein:
X is halogen, and
R is formula VI or VII

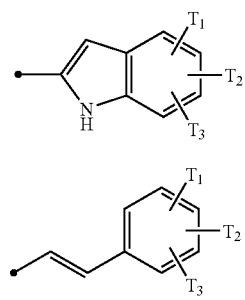

Formula VI

Formula VII wherein each $T_1$, $T_2$, and $T_3$ is independently $OR^5$, $NR^5{}_2$, $NHCOR^5$, or $O(CH_2)_n NR^5{}_2$, where each $R^5$ independently represents H, a $C_{1-6}$ alkyl optionally substituted with one or more hydroxy or amino groups, and each n is independently 1, 2, 3, or 4, and
• represents the point of attachment of R to Formula I defined above, and
wherein ligands L1–L4 represent one of the tetradentate ligands IX or X

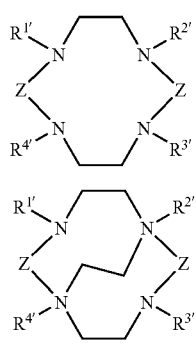

Formula IX

Formula X wherein each $R^{1'}$ to $R^{4'}$ independently represents H, Me, $CH_2(CH_2)_n SO_3H$, $CH_2(CH_2)_n CO_2H$, $CH_2(CH_2)_n OP(O)(OH)_2$, or $CH_2(CH_2)_n NMe_2$, where each n is independently 1, 2, 3, or 4, each Z is independently $-(CH_2)_2-$ or $-(CH_2)_3-$, and wherein the overall charge of the complex is neutral, positive, or negative and wherein in the case of a non-neutral complex $F^{countercharge}$ is selected from a range of physiologically acceptable counterions, including halide⁻, $NO_3{}^-$, $NH_4{}^-$, or $Na^+$, and wherein q is the required number to neutralize the overall charge on the complex; or an enantiomer, a diastereomer or a physiologically functional salt thereof.

2. The metal complex according to claim 1 wherein R is selected from one of

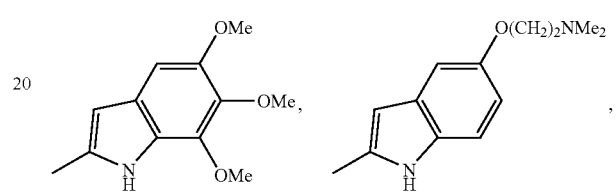

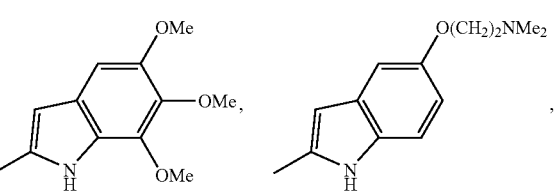

3. The metal complex according to claim 1 wherein X is Cl.

4. The metal complex according to claim 1 selected from one of the following;

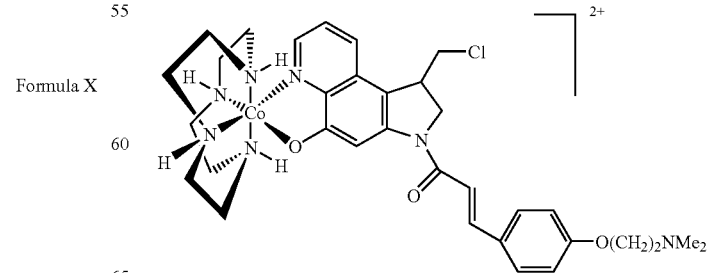

-continued

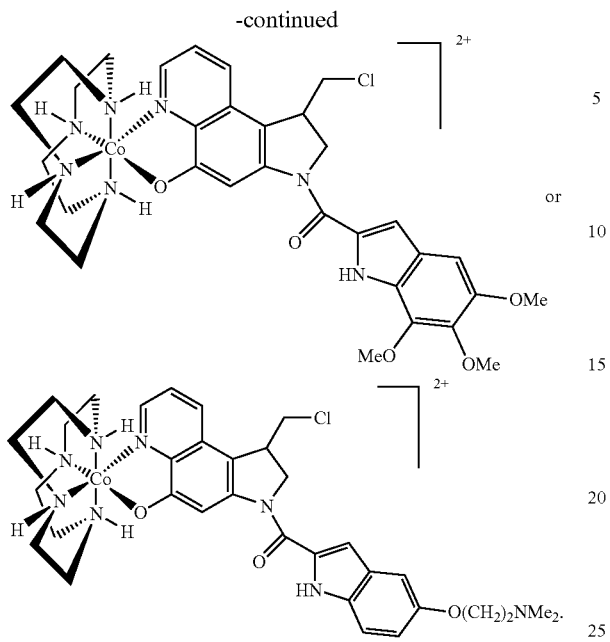

5. A method of providing cancer treatment, which includes the steps of
   (a) administering to a patient in need of such therapy an effective amount of a metal complex of Formula I as defined in claim 1, and
   (b) activating the metal complex of Formula I under hypoxic conditions via reduction, either enzymatically or by a non-enzymatic endogenous reducing agents, or by ionizing radiation,
   wherein said activation releases a sufficient amount of an effector from said metal complex of Formula I.

6. The method according to claim 5 including the alternative step of activation of the metal complex of Formula I as defined above by radiotherapy radiation.

7. A composition comprising as an active agent a metal complex of Formula I as defined in claim 1 and a pharmaceutically acceptable excipient, adjuvant or carrier.

8. A method of preparing a metal complex according to claim 1 comprising the step of coupling an 8-quinoline heterocyclic compound of Formula XIX'

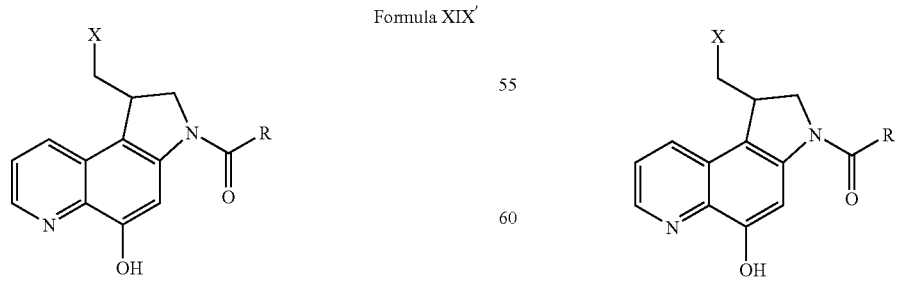

wherein:
X is halogen, and
R is formula VI or VII

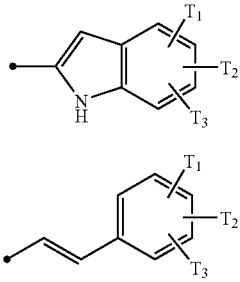

Formula VI

Formula VII wherein each $T_1$, $T_2$, and $T_3$ is independently $OR^5$, $NR^5{}_2$, $NHCOR^5$, or $O(CH_2)_n NR^5{}_2$, where each $R^5$ independently represents H, a $C_{1-6}$ alkyl optionally substituted with one or more hydroxy or amino groups, and each n is independently 1, 2, 3, or 4, and

• represents the point of attachment of R to Formula XIX' defined above, or an enantiomer, a diastereomer or a physiologically functional salt thereof, with one of the tetradentate ligands VI or VII

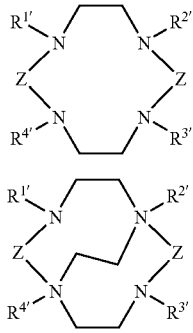

Formula VI

Formula VII wherein each $R^{1'}$ to $R^{4'}$ independently represents H, Me, $CH_2(CH_2)_n SO_3H$, $CH_2(CH_2)_n CO_2H$, $CH_2(CH_2)_n OP(O)(OH)_2$, or $CH_2(CH_2)_n NMe_2$, where each n is independently 1, 2, 3, or 4, each Z is independently $-(CH_2)_2-$ or $-(CH_2)_3-$, and wherein the ligands are complexed to Co.

9. A method of preparing an 8-quinoline heterocyclic compound of Formula XIX' wherein:
X is halogen, and
R is formula VI or VII

Formula VI

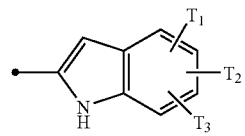

Formula VII

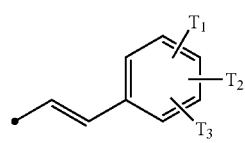

wherein each $T_1$, $T_2$, and $T_3$ is independently $OR^5$, $NR^5{}_2$, $NHCOR^5$, or $O(CH_2)_nNR^5{}_2$, where each $R^5$ independently represents H, a $C_{1-6}$ alkyl optionally substituted with one or more hydroxy or amino groups, and each n is independently 1, 2, 3, or 4, and
• represents the point of attachment of R to Formula XIX' defined above, or an enantiomer, a diastereomer or a physiologically functional salt thereof, comprising the following reaction pathway 10. The method according to claim 9 including the further steps represented by the pathway:

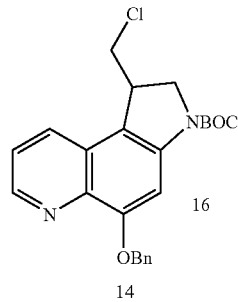

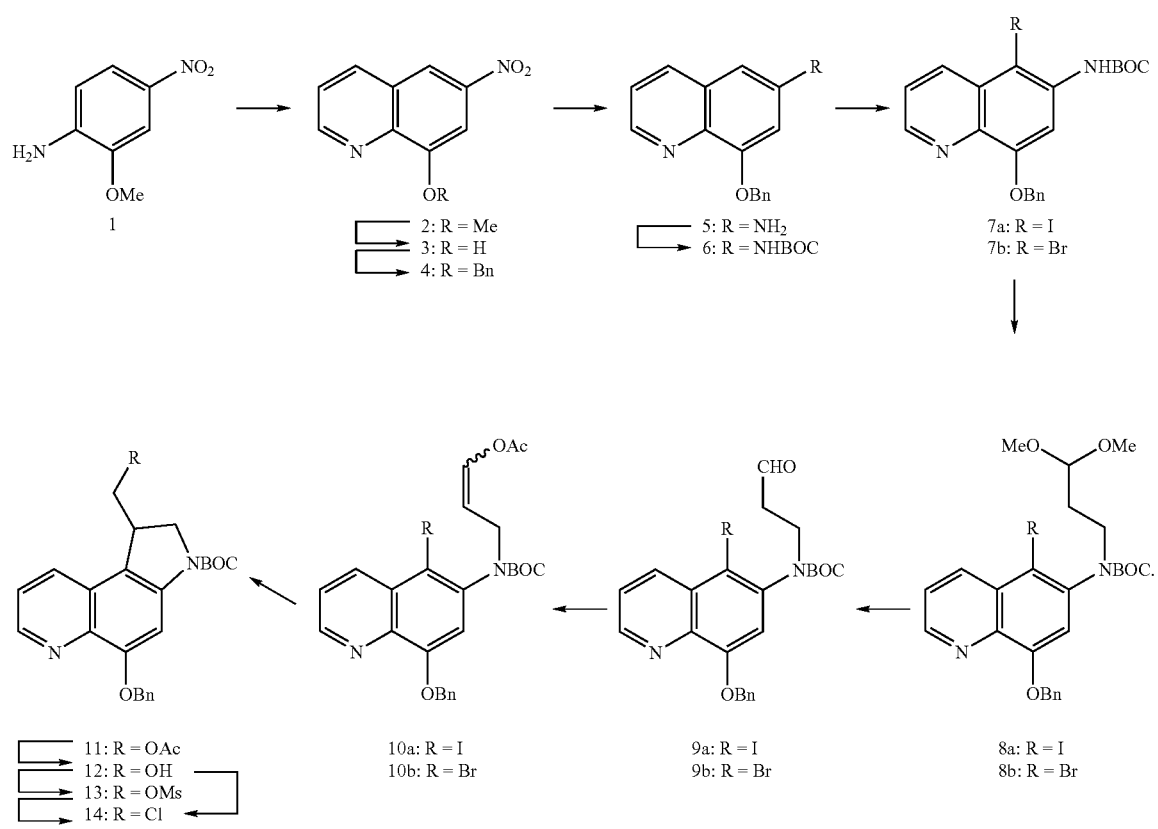

-continued
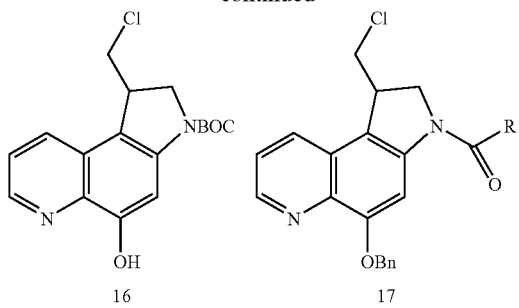
16  17
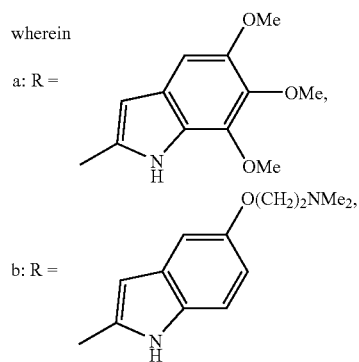
18a–f
wherein
a: R = 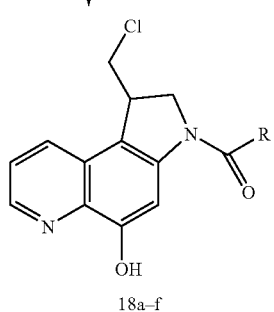
b: R =
c: R = 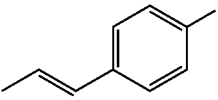
d: R = 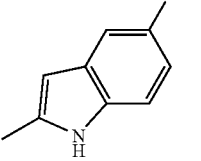
e: R = 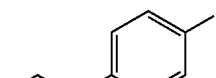 and
f: R = 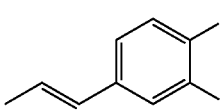
* * * * *